(12) United States Patent
Fiebig et al.

(10) Patent No.: US 8,128,935 B2
(45) Date of Patent: Mar. 6, 2012

(54) DNA SEQUENCE AND RECOMBINANT PRODUCTION OF THE GRASS POLLEN ALLERGEN PHL P 4

(75) Inventors: Helmut Fiebig, Schwarzenbek (DE); Andreas Nandy, Hamburg (DE); Roland Suck, Hamburg (DE); Oliver Cromwell, Wentorf (DE); Arnd Petersen, Bad Segeberg (DE); Wolf-Meinhard Becker, Mozen (DE)

(73) Assignee: Merck Patent GmbH, Darmstadt (DE)

( * ) Notice: Subject to any disclaimer, the term of this patent is extended or adjusted under 35 U.S.C. 154(b) by 615 days.

(21) Appl. No.: 10/518,927

(22) PCT Filed: Jun. 11, 2003

(86) PCT No.: PCT/EP03/06092
§ 371 (c)(1),
(2), (4) Date: Dec. 23, 2004

(87) PCT Pub. No.: WO04/000881
PCT Pub. Date: Dec. 31, 2003

(65) Prior Publication Data
US 2006/0177470 A1    Aug. 10, 2006

(30) Foreign Application Priority Data
Jun. 25, 2002   (EP) ..................................... 02013953

(51) Int. Cl.
| A61K 38/00 | (2006.01) |
| A61K 39/00 | (2006.01) |
| A61K 39/35 | (2006.01) |
| A61K 39/36 | (2006.01) |
| A01N 37/18 | (2006.01) |
| C07K 1/00 | (2006.01) |
| C07K 14/00 | (2006.01) |
| C07K 17/00 | (2006.01) |

(52) U.S. Cl. ................... 424/185.1; 424/275.1; 514/1.1; 530/350

(58) Field of Classification Search ........................ None
See application file for complete search history.

(56) References Cited

U.S. PATENT DOCUMENTS
2003/0135888 A1* 7/2003 Zhu et al. ....................... 800/288

OTHER PUBLICATIONS

Fischer et al. 'Characterization of Phl p 4, a major timothy grass (Phleum pratense) pollen allergen.' J. Allerg. Clin. Immunol. 98(1):189-198, 1996.*
Metzler et al. 'Solution structure of human CTLA-4 and delineation of a CD80/CD86 binding site conserved in CD28.' Nature Structural Biol. 4:527-531, 1997.*
Bowie et al. Decipering the Message in Protein Sequences: Tolerance to Amino Acid Substitutions. Science 247:1306-1310, 1990.*
Kuby et al. 'Immunology.' Fourth Edition, Chapter 18: 449-465.*
Colman et al. 'Effects of amino acid sequence changes on antibody-antigen interactions.' Research in Immunology 145(1):33-36, 1994.*
Abaza et al. Effects of amino acid substitutions outside an antigenic site on protein binding to monoclonal antibodies of predetermined specificity obtained by peptide immunization: demonstration with region 94-100 (antigenic site 3) of myoglobin.° J. Prot. Chem. 11(5):433-444, 1992.*
Lederrnan et al. 'A single amino acid substitution in a common African allele of the CD4 molecule ablates binding of the monoclonal antibody, OKT4.' Molec. Immunolo 28:1171-1181, 1991.*
Blumenthal et al. 'Definition of an Allergen.' Allergens and Allergen Immunotherapy. Ed. R Lockey, S. Bukantz and J. Bousquet. New York: Marcel Decker, 2004.37-50.*
Kinnunen et al. 'Potential of an altered peptide ligand of lipocalin allergen Bos d 2 for peptide immunotherapy.' J. Allergy Clin Immunol. 119(4):965-972, 2007.*
Tarzi et al. 'Peptide immunotherapy for allergic disease.' Expert. Opin. Biol. Ther. 3(4):617-626, 2003.*
Kuby et al. 'Immunology.' W H Freeman & Co (Sd); 4th edition, Chapter 18: 449-465, Jan. 15, 2000.*
Suck R et al: "The high molecular mass allergen fraction of timothy grass pollen (Phleum pratense) between50-60 kDa is comprised of two major allergens: Ph1 p4 and Ph1 p13" Clinical and Experimetnal Allergy, Bd. 30, Nr. 10, Oct. 2000, XP002260344.
Haavik et al. "Glycoprotein allergens in pollen of timothy. II. Isolation and characterization of a basic glycoprotein allergen." Int Arch Allergy Appl Immunol. 1985;78(3):260-8 (Abstract Only).
Fahlbusch B et al: Detection and quantification of group 4 allergens in grass pollen extracts using monoclonal antibodies Clinical and Experimental Allergy, Bd. 28, Nr. 7 Jul. 1998, 799-807, XP002260345.
Suck R et al: "Complementary DNA Cloning and expression of a newly recognized highmolecular mass allergen Phl P 13 from Timothy Grass pollen (Phleum pratense)" Clinical and experimental allergy, Blackwell scientific publications, London, GB, Bd. 30, Nr. 3, Mar. 2000, 324-332, XP000953168. Stumvoll Sabine et al: "Purification, structural and immunological characterization of a timothy grass (Phleum pratense) pollen allergen, Ph1 p4, with cross-reactive potential." Biological Chemistry, Bd. 383, Nr. 9, Sep. 2002 1383-1396, XP002260346.
Valenta et al. "Diagnosis of Grass Pollen Allergy with Recombinant Timothy Grass (Phleum pretense) Pollen Allergens." Int Arch Allergy Immunol 1992;97:287-294. (Abstract Only).

* cited by examiner

Primary Examiner — Nora Rooney
(74) Attorney, Agent, or Firm — Millen, White, Zelano, Branigan, P.C.

(57) ABSTRACT

The present invention relates to the provision of the genetic sequence of the major grass pollen allergen Phl p 4. The invention also covers fragments, new combinations of partial sequences and point mutants having a hypoallergenic action. The recombinant DNA molecules and the derived polypeptides, fragments, new combinations of partial sequences and variants can be utilised for the therapy of pollen-allergic diseases. The proteins prepared by recombinant methods can be employed for the in vitro and in vivo diagnosis of pollen allergies.

6 Claims, 5 Drawing Sheets

Fig. 1      Internal DNA sequence of the Phl p 4 gene

```
C A C C G G A A G G G G G T G C T G T T C A A C A T C C A G T A C G T C A A
C T A C T G G T T C G C C C C G G G A G C C G G C G C G G C G C C A T T G T
C G T G G A G C A A G G A G A T C T A C A A C T A C A T G G A G C C G T A C
G T G A G C A A G G A C C C C G T C C A G G C C T A C G C C A A C T A
```

Fig. 2   3' end of the nucleic acid sequence of the Phl p 4 gene

```
A C T A C T G G T T C G C C C C G G G A G C C G G C G C G G C
G C C A T T G T C G T G G A G C A A G G A G A T C T A C A A C
T A C A T G G A G C C A T A C G T G A G C A A G A A C C C C A
G G C A G G C C T A C G C C A A C T A C A G G G A C A T C G A
C C T C G G G A G G A A C G A G G T G G T G A A C G A C G T C
T C C A C C T T C A G C A G C G G T T T G G T G T G G G C C
A G A A A T A C T T C A A G G G C A A C T T C C A G A G G C T
C G C C A T C A C C A A G G G C A A G G T G G A T C C C A C C
G A C T A C T T C A G G A A C G A G C A G A G C A T C C C G C
C G C T C A T C A A A A A G T A C T G A
```

Fig. 3  Localisation of Phl p 4 peptides in the deduced amino acid sequence of the Phl p 4 allergen

```
  1  Y F P P P A A K E D F L G C L V K E I P P R L L Y A K S S P A Y P S V L G Q T I
     Y F P P P A A K E D F L G X L V K E I P P R L L Y A K S S P A Y P
                              Peptide P1

41  R N S R W S S P D N V K P I Y I V T P T N A S H I Q S A V V C G R R H G V R I R

81  V R S G G H D Y E G L S Y R S L Q P E E F A V V D L S K M R A V W V D G K A R T
                              G L X Y R X L X P E
                              Peptide P3

121  A W V D S G A Q L G E L Y Y A I H K A S T V L A F P A G V C P T I G V G G N F A

161  G G G F G M L L R K Y G I A A E N V I D V K L V D A N G T L H D K K S M G D D H
                                                                  K X M G D D H
                                                                   Peptide P4

201  F W A V R G G G E S F G I V V A W K V R L L P V P P T V T V F K I P K K A S E
     F X A V R                                                              A P E

241  G A V D I I N R W Q V V A P Q L P D D L M I R V I A Q G P T A T F E A M Y L G T
     G A V D I I
     Peptide P5

281  C Q T L T P M M S S K F P E L G M N A S H C N E M S W I Q S I P F V H L G H R D

321  N I E D D L L N R N N T F K P F A E Y K S D Y V Y E P F P K R V W E Q I F S T W

361  L L K P G A G I M I F D P Y G A T I S A T P E W A T P F P H R K G V L F N I Q Y
                                        S A T P F X H R K G V L F N I Q Y
                                                                Peptide P2

401  V N Y W F A P G A G A A P L S W S K E I Y N Y M E P Y V S K N P R Q A Y A N Y R
     V                                        M E P Y V S I N P V Q A Y A N Y
                                                                Peptide P6

441  D I D L G R N E V V N D V S T F S S G L V W G Q K Y F K G N F Q R L A I T K G K

481  V D P T D Y F R N E Q S I P P L I K K Y .
```

Fig. 4   Determination of the identity of recombinant Phl p 4 (rPhl p 4) by means of the monoclonal antibodies 5H1 (blot A) and 3C4 (blot B) by Western blot
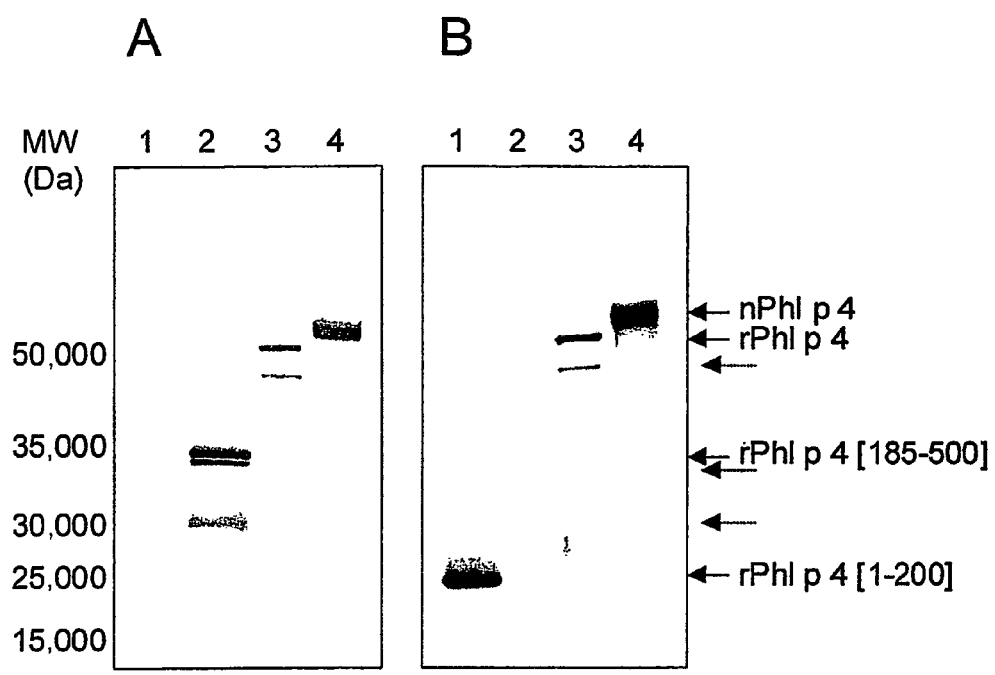

Fig. 5   Determination of the reactivity of recombinant Phl p 4 (rPhl p 4) with IgE from sera of grass pollen allergy sufferers by Western blot
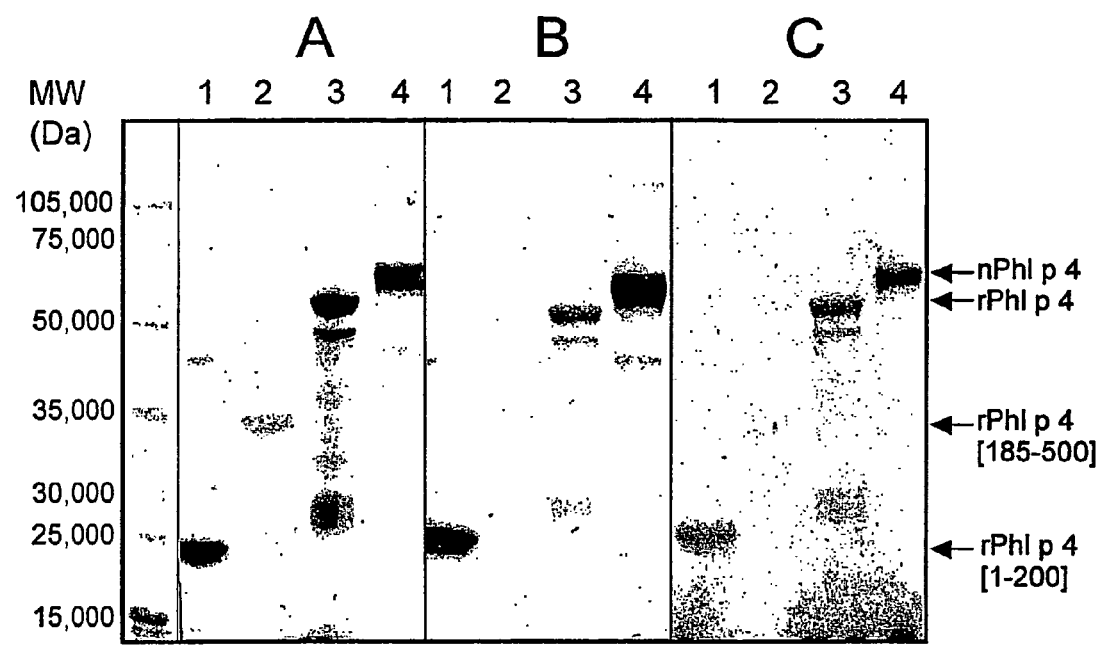

DNA SEQUENCE AND RECOMBINANT PRODUCTION OF THE GRASS POLLEN ALLERGEN PHL P 4

This application is the US national phase under §371 of PCT/EP03/06092, filed Jun. 11, 2003, and claims priority to EP 02013953.1, filed Jun. 25, 2002.

BACKGROUND OF THE INVENTION

The present invention relates to the provision of the genetic sequence of the major grass pollen allergen Phl p 4. The invention also covers fragments, new combinations of partial sequences and point mutants having a hypoallergenic action. The recombinant DNA molecules and the derived polypeptides, fragments, new combinations of partial sequences and variants can be utilised for the therapy of pollen-allergic diseases. The proteins prepared by recombinant methods can be employed for the in vitro and in vivo diagnosis of pollen allergies.

Type 1 allergies are of importance worldwide. Up to 20% of the population in industrialised countries suffer from complaints such as allergic rhinitis, conjunctivitis or bronchial asthma. These allergies are caused by allergens present in the air (aeroallergens) which are liberated from sources of various origin, such as plant pollen, mites, cats or dogs. Up to 40% of these type 1 allergy sufferers in turn exhibit specific IgE reactivity with grass pollen allergens (Freidhoff et al., 1986, J. Allergy Clin. Immunol. 78, 1190-2001).

The substances which trigger type 1 allergy are proteins, glycoproteins or polypeptides. After uptake via the mucous membranes, these allergens react with the IgE molecules bonded to the surface of mast cells in sensitised individuals. If two IgE molecules are crosslinked to one another by an allergen, this results in the release of mediators (for example histamine, prostaglandins) and cytokines by the effector cell and thus in the corresponding clinical symptoms.

A distinction is made between major and minor allergens depending on the relative frequency with which the individual allergen molecules react with the IgE antibodies of allergy sufferers.

In the case of timothy grass (*Phleum pretense*), Phl p 1 (Petersen et al., 1993, J. Allergy Clin. Immunol. 92: 789-796), Phl p 5 (Matthiesen and Löwenstein, 1991, Clin. Exp. Allergy 21: 297-307; Petersen et al., 1992, Int. Arch. Allergy Immunol. 98: 105-109), Phl p 6 (Petersen et al., 1995, Int. Arch. Allergy Immunol. 108, 49-54). Phl p 2/3 (Dolecek et al., 1993, FEBS 335 (3), 299-304), Phl p 4 (Haavik et al., 1985, Int. Arch. Allergy Appl. Immunol. 78: 260-268; Valenta et al., 1992, Int. Arch. Allergy Immunol. 97: 287-294, Fischer et al., 1996, J. Allergy Clin. Immunol. 98: 189-198) and Phl p 13 (Suck et al., 2000, Clin. Exp. Allergy 30: 324-332; Suck et al., 2000, Clin. Exp. Allergy 30: 1395-1402) have hitherto been identified as major allergens.

Phl p 4 has been mentioned as a basic glycoprotein having a molecular weight of between 50 and 60 kDa (Haavik et al., 1985, Int. Arch. Allergy Appl. Immunol. 78: 260-268). The Phl p 4 molecule is trypsin-resistant (Fischer et al., 1996, J. Allergy Clin. Immunol. 98: 189-198), and 70-88% of grass pollen allergy sufferers have IgE antibodies against this molecule (Valenta et al., 1993, Int. Arch. Allergy Immunol. 97: 287-294; Rossi et al., 2001, Allergy 56:1180-1185; Mari, 2003, Clin. Exp. Allergy 33:43-51). Homologous molecules have been described from related grass species (Su et al., 1991, Clin. Exp. Allergy 21: 449-455; Jaggi et al., 1989, Int. Arch. Allergy Appl. Immunol. 89: 342-348; Jaggi et al., 1989, J. Allergy Clin. Immunol. 83: 845-852; Leduc-Brodard et al., 1996, J. Allergy Clin. Immunol. 98:1065-1072; 14-17). These homologous molecules of the *Poaceae* form allergen group 4, whose molecules have high immunological cross-reactivity with one another both with monoclonal mouse antibodies and with human IgE antibodies (Fahlbusch et al., 1993 Clin. Exp. Allergy 23:51-60; Leduc-Brodard et al., 1996, J. Allergy Clin. Immunol. 98:1065-1072; Su et al., 1996, J. Allergy Clin. Immunol. 97:210; Fahlbusch et al., 1998, Clin. Exp. Allergy 28:799-807; Gavrović-Jankulović et al., 2000, Invest. Allergol. Clin. Immunol. 10 (6): 361-367; Stumvoll et al. 2002, Biol. Chem. 383: 1383-1396; Grote et al., 2002, Biol. Chem. 383: 1441-1445; Andersson and Lidholm, 2003, Int. Arch. Allergy Immunol. 130: 87-107; Mari, 2003, Clin. Exp. Allergy, 33 (1): 43-51).

In contrast to the above-mentioned major allergens of *Phleum pratense* (Phl p 1, Phl p 2/3, Phl 5a and 5b, Phl p 6 and Phl p 13), the primary structure of Phl p 4 has not yet been elucidated. Likewise, there is no complete sequence of molecules from group 4 from other grass species.

The determination of the N-terminal amino acid sequence was hitherto unsuccessful. However, the causes of this are not known. Fischer et al. (J. Allergy Clin. Immunol., 1996; 98: 189-198) assume N-terminal blocking, but were able to purify an internal peptide after degradation with lysyl endopeptidase and to determine its sequence: IVALPXG-MLK (SEQ ID NO 7).

This peptide has homologies to peptide sequences in the ragweed allergens Amb a1 and Amb a2 and similarities to sequences in proteins from maize (Zm58.2), tomato (lat 59, lat 56) and tobacco (G10) (Fischer et al., 1996, J. Allergy Clin. Immunol. 98: 189-198). For *Lolium perenne*, peptide fragments having the following sequence have been described for the basic group 4 allergen: FLEPVLGLIFPAGV (SEQ ID NO 8) and GLIEFPAGV (SEQ ID NO 9) (Jaggi et al., 1989, Int. Arch. Allergy Appl. Immunol. 89: 342-348).

Peptides have likewise been obtained from the group 4 allergen from *Dactylus glomerata* by enzymatic degradation and sequenced:
DIYNYMEPYVSK (P15, SEQ ID NO 10),
VDPTDYFGNEQ (P17, SEQ ID NO 11),
ARTAWVDSGAQLGELSY (P20, SEQ ID NO 12)
and GVLFNIQYVNYWFAP (P22, SEQ ID NO 13) (Leduc-Brodard et al., 1996, J. Allergy Clin. Immunol. 98: 1065-1072).

Peptides have also been obtained from the group 4 allergen of subtropical Bermuda grass (*Cynodon dactylon*) by proteolysis and sequenced:
KTVKPLYIITP (S, SEQ ID NO 14),
KQVERDFLTSLTKDIPQLYLKS (V49L, SEQ ID NO 15),
TVKPLYIITPITAAMI (T33S, SEQ ID NO 16),
LRKYGTAADNVIDAKWDAQGRLL (T35L, SEQ ID NO 17),
KWQTVAPALPDPNM (P2, SEQ ID NO 18),
VTWIESVPYIPMGDK (V26L, SEQ ID NO 19),
GTVRDLLXRTSNIKAFGKY (L25L, SEQ ID NO 20),
TSNIKAFGKYKSDYVLEPIPKKS (T22L, SEQ ID NO 21),
YRDLDLGVNQWG (P3, SEQ ID NO 22),
SATPPTHRSGVLFNI (V20L, SEQ ID NO 23),
and AAAALPTQVTRDIYAFMTPYVSKN-PRQAYVNYRDLD (V14L, SEQ ID NO 24) (Liaw et al., 2001, Biochem. Biophys. Research Communication 280: 738-743).

However, these described peptide sequences for Phl p 4 and group 4 allergens have hitherto not resulted in the elucidation of the complete primary structure of group 4 allergens.

The object on which the present invention is based therefore comprised the provision of the complete DNA sequence of Phl p 4 and of a corresponding recombinant DNA on the basis of which the Phl p 4 allergen can be expressed as protein and made available for pharmacologically significant utilisation as such or in modified form.

LIST OF FIGURES

FIG. 1: Internal DNA sequence (SEQ ID NO 25) of the Phl p 4 gene Amplicons obtained with genomic DNA were cloned with the degenerated primers No. 30 (sense) and No. 37 (antisense), both shown in italics, and sequenced. The sequence shown represents the consensus from 6 clones. The specific sense primer No. 82 created from this sequence is shown underlined.

FIG. 2: 3' end of the nucleic acid sequence (SEQ ID NO 26) of the Phl p 4 gene

Amplicons were obtained with the specific sense primer No. 82 (shown in italics) and an anchor primer in a 3'-RACE PCR with *Phleum pratense* cDNA and sequenced. The sequence shown represents the consensus from 3 sequencing processes and covers the 3' end of the Phl p 4 gene to the stop codon (double underlined). The sequence ranges employed for construction of the antisense primers No. 85 and No. 86 are shown underlined.

FIG. 3: Localisation of the Phl p 4 peptides in the deduced amino acid sequence of the Phl p 4 allergen (SEQ ID NO 2)

The peptides P1-P6 (SEQ ID NO's 27-32) obtained from the amino acid sequencing of the purified and fragmented Phl p 4 allergen can unambiguously be assigned to the amino acid sequence of the Phl p 4 gene derived from the nucleic acid sequence.

FIG. 4: Determination of the identity of recombinant Phl p 4 (rPhl p 4) by means of monoclonal antibodies 5H1 (blot A) and 3C4 (blot B) specific for nPhl p 4 by Western blot.
Track 1: *E. coli* total cell extract comprising rPhl p 4 fragment 1-200
Track 2: *E. coli* total cell extract comprising rPhl p 4 fragment 185-500
Track 3: *E. coli* total cell extract comprising rPhl p 4
Track 4: purified nPhl p 4 from *Phleum pratense*
(←): termination or degradation fragments of C-terminal rPhl p 4 fragment or rPhl p 4 entire molecule FIG. 5: Determination of the reactivity of recombinant Phl p 4 (rPhl p 4) using IgE from sera of grass pollen allergy sufferers by Western blot. Extracts of transformed *E. coli* cells which either express the complete Phi p 4 gene or the N-terminal fragment 1-200 or the C-terminal fragment 185-500 were separated in the SDS-PAGE and transferred to nitrocellulose membranes. The blot was incubated with sera from grass pollen-allergic donor A, B or C, and bound IgE was subsequently detected calorimetrically via an anti-human IgE antibody conjugated with alkaline phosphatase.
Track 1: *E. coli* total cell extract comprising rPhl p 4 fragment 1-200
Track 2: *E. coli* total cell extract comprising rPhl p 4 fragment 185-500
Track 3: *E. coli* total cell extract comprising rPhl p 4
Track 4: purified nPhl p 4 from *Phleum pratense*

The numbers used above and below for nucleotide or amino acid sequences "SEQ ID NO" relate to the sequence protocol attached to the description.

DESCRIPTION OF THE INVENTION

The present invention now provides for the first time the genetic sequence of the major grass pollen allergen Phl p 4, with three dominant sequences (SEQ ID NO 1, 3 and 5) arising from the single nucleotide polymorphisms (SNPs) found.

The present invention therefore relates to a DNA molecule corresponding to a nucleotide sequence selected from a group consisting of SEQ ID NO 1, SEQ ID NO 3 and SEQ ID NO 5 or a DNA molecule corresponding to a nucleotide sequence which encodes for the major allergen Phl p 4 from *Phleum pratense*.

The invention also covers fragments, new combinations of partial sequences and point mutants having a hypoallergenic action.

The invention therefore furthermore relates to corresponding partial sequences, a combination of partial sequences or exchange, elimination or addition mutants which encode for an immunomodulatory, T-cell-reactive fragment of a group 4 allergen of the *Poaceae*.

In addition to the group 4 allergens of the other grass species, the group 13 allergens are also of interest in connection with the present invention since they exhibit a very similar molecular weight to the group 4 allergens in the SDS-PAGE and are difficult to separate by biochemical techniques (Suck et al., 2000, Clin. Exp. Allergy 30: 324-332, Suck et al., 2000, Clin. Exp. Allergy 30: 1395-1402). With the aid of the protein and DNA sequence according to the invention which is now available for the first time, however, it can unambiguously be shown that groups 4 and 13 have significantly different amino acid sequences.

With knowledge of the DNA sequence of naturally occurring allergens, it is now possible to prepare these allergens as recombinant proteins which can be used in the diagnosis and therapy of allergic diseases (Scheiner and Kraft, 1995, Allergy 50: 384-391).

A classical approach to effective therapeutic treatment of allergies is specific immunotherapy or hyposensitisation (Fiebig, 1995, Allergo J. 4 (6): 336-339, Bousquet et al., 1998, J. Allergy Clin. Immunol. 102(4): 558-562). In this method, the patient is injected subcutaneously with natural allergen extracts in increasing doses. However, there is a risk in this method of allergic reactions or even anaphylactic shock. In order to minimise these risks, innovative preparations in the form of allergoids are being employed. These are chemically modified allergen extracts which have significantly reduced IgE reactivity, but identical T-cell reactivity compared with the untreated extract (Fiebig, 1995, Allergo J. 4 (7): 377-382).

Even more substantial therapy optimisation would be possible with allergens prepared by recombinant methods. Defined cocktails of high-purity allergens prepared by recombinant methods, optionally matched to the individual sensitisation patterns of the patients, could replace extracts from natural allergen sources since these, in addition to the various allergens, contain a relatively large number of immunogenic, but non-allergenic secondary proteins.

Realistic perspectives which may result in reliable hyposensitisation with expression products are offered by specifically mutated recombinant allergens in which IgE epitopes are specifically deleted without impairing the T-cell epitopes which are essential for therapy (Schramm et al., 1999, J. Immunol. 162: 2406-2414).

A further possibility for therapeutic influencing of the disturbed TH-cell equilibrium in allergy sufferers is immunotherapeutic DNA vaccination. This involves treatment with expressable DNA which encodes for the relevant allergens.

Initial experimental evidence of allergen-specific influencing of the immune response has been furnished in rodents by injection of allergen-encoding DNA (Hsu et al., 1996, Nature Medicine 2 (5): 540-544).

The present invention therefore also relates to a DNA molecule described above or below or a corresponding recombinant expression vector as medicament.

The corresponding proteins prepared by recombinant methods can be employed for the therapy and for the in vitro and in vivo diagnosis of pollen allergies.

For preparation of the recombinant allergen, the cloned nucleic acid is ligated to an expression vector, and this construct is expressed in a suitable host organism. After biochemical purification, this recombinant allergen is available for the detection of IgE antibodies by established methods.

The present invention therefore furthermore relates to a recombinant expression vector comprising a DNA molecule described above or below, functionally linked to an expression control sequence and a host organism transformed with the said DNA molecule or the said expression vector.

The invention likewise relates to the use of at least one DNA molecule described above or at least one expression vector described above for the preparation of a medicament for immunotherapeutic DNA vaccination of patients having allergies in the triggering of which group 4 allergens of the Poaceae are involved and/or for the prevention of such allergies.

As already stated, the invention can be used as an essential component in a recombinant allergen- or nucleic acid-containing preparation for specific immunotherapy. There are a number of possibilities here. Firstly, the protein with an unchanged primary structure may be a constituent of the preparation. Secondly, through specific deletion of IgE epitopes of the entire molecule or the preparation of individual fragments which encode for T-cell epitopes, a hypoallergenic (allergoidal) form can be used in accordance with the invention for therapy in order to prevent undesired side effects. Finally, the nucleic acid per se, if ligated with a eukaryotic expression vector, gives a preparation which on direct application modifies the allergic immune state in the therapeutic sense.

The invention thus relates to recombinant DNA molecules corresponding to SEQ ID NO 1, 3 or 5, where the nucleotide sequence of positions 1-69 has been derived from the amino acid sequence of the Phl p 4 N-terminus. Codons which frequently occur in *E. coli* were used here. From position 70, the DNA sequence corresponds to that which has been identified in genomic and cDNA of *Phleum pratense*.

The present invention therefore furthermore relates to a DNA molecule comprising a nucleotide sequence according to SEQ ID NO 1, SEQ ID NO 3 or SEQ ID NO 5, commencing with position 70, which encodes for a polypeptide having the properties of the major allergen Phl p 4 from *Phleum pratense*.

Furthermore, the present invention relates to the polypeptides encoded by one or more of the above-described DNA molecules, preferably in their property as medicament.

These are, in particular, polypeptides according to SEQ ID NO 2, SEQ ID NO 4 or SEQ ID NO 6, where amino acid positions 1-33 have been determined by N-terminal amino acid sequencing of the isolated natural Phl p 4 allergen. Positions 24-500 were derived from the DNA sequence according to SEQ ID NO 1, 3 and 5. Variable amino acids at positions 6, 7, 8 and 9 originate from the N-terminal protein sequencing of various preparations of natural Phl p 4 (Table 1).

Accordingly, the invention also relates to a process for the preparation of polypeptides of this type by cultivation of a host organism according to Claim 11 and isolation of the corresponding polypeptide from the culture.

The invention likewise relates to the use of at least one polypeptide described above for the preparation of a medicament for the diagnosis and/or treatment of allergies in the triggering of which group 4 allergens of the *Poaceae* are involved and for the prevention of such allergies.

These polypeptides or proteins according to the invention which act as allergens for humans are present in the pollen grains of *Phleum pratense*. The pollen grains of the other *Poaceae* species, such as, for example, *Lolium perenne, Dactylis glomerata, Poa pratensis, Cynodon dactylon, Holcus lanatus*, inter alia, contain homologous allergen molecules (group 4 allergens).

The homology of these molecules has been demonstrated through their immunological cross-reactivity both with murine monoclonal antibodies and also with human IgE antibodies.

Consequently, the invention also relates to sequences which are homologous to the Phl p 4 DNA sequence and corresponding DNA molecules of group 4 allergens from other *Poaceae* such as, for example, *Lolium perenne, Dactylis glomerata, Poa pratensis, Cynodon dactylon, Holcus lanatus, Triticum aestivum* and *Hordeum vulgare*, which, owing to the sequence homology which exists, hybridise with Phl p 4 DNA under stringent conditions or have immunological cross-reactivity with respect to Phl p 4.

The following procedure was followed in the determination of the protein and DNA sequence of Phl p 4:

The natural allergen Phl p 4 was purified and isolated by described methods (Fahlbusch et al. 1998, Clin. Exp. Allergy 28: 799-807, Suck et al. 2000, Clin. Exp. Allergy 30: 1395-1402). The micropurification and the removal of traces of the group 13 allergen was carried out by the method described by Suck et al. (2000, Clin. Exp. Allergy 30: 1395-1402). The N-terminal amino acid sequence of this Phl p 4 isolated from *Phleum pretense* was determined by means of Edman degradation. The N-terminal sequences (P1a-f shown in Table 1 were determined with various batches of Phl p 4. The consensus sequence for the first 15 positions is regarded as being the following sequence: YFPP'P'AAKEDFLGXL (SEQ ID NO 33). Position 14 could not be determined; it is probably occupied by cysteine. The different amino acids in positions 6, 7, 8 and 9 in the different batches indicate variations in the sense of isoforms. Positions 4 and 5 are occupied by hydroxyproline (P'), which was unambiguously determined by specific analysis in the analyses of preparations p1-a and -b.

Treatment of the SDS-denatured Phl p 4 with the endopeptidase Glu-C (Promega, Heidelberg, Germany) gave various peptides. The amino acid sequences shown in Table 1 were determined for two peptides (P2 and P3). 2 peptides (P4 and P5) were purified by cleavage using the endopeptidase Lys-C (Roche, Mannheim, Germany) and sequenced (Table 1). A further peptide (P6) was isolated by CNBr cleavage and the amino acid sequence was determined (Table 1).

The amino acid sequences of the N-terminal sequence and the internal peptides 2 and 6 were used as the basis for the construction of degenerated primers. Amplicons were prepared with the sense primer No. 30 and the antisense primer No. 37 (Table 2) using genomic DNA from *Phleum pratense*. The clones obtained from these amplicons were sequenced (FIG. 1) and used for the construction of the specific sense primer No. 82 (Table 2). Using a cDNA prepared from the representative mRNA population from *Phleum pretense* pollen and the specific sense primer No. 82 according to the invention and the anchor primer AUAP (Life Technologies, Karlsruhe, Germany), a PCR was carried out under stringent conditions. This approximately 450 kb amplicon was sequenced and the missing sequence as far as the 3' end of the Phl p 4 gene was thus identified (FIG. 2). Based on this C-terminal Phl p 4 sequence determined in accordance with the invention, the specific antisense primers No. 85 and No. 86 were constructed (Table 2). Based on the N-terminal amino acid sequence of the Phl p 4 peptide P1-a (Table 1), the degenerated sense primer No. 29, derived from the DNA encoding for amino acid positions 24-33 (LYAKSSPAYP (SEQ ID NO 34)), was constructed.

A PCR was carried out with primers No. 29 and No. 86 using genomic *Phleum pratense* DNA. This PCR product was employed as the basis for a second PCR (nested PCR) with primers No. 29 and No. 85. The amplicons were inserted into the vector pGEM T-easy (Promega, Heidelberg, Germany), cloned and sequenced. This sequence begins at position 24 calculated from the N-terminus or position 70 of the DNA sequence in accordance with SEQ ID NO 1, 3 or 5 and extends to primer No. 85 (position 1402 in SEQ ID NO 1, 3 or 5), which is localised in the already determined C-terminal section of the Phl p 4 gene. Using these data, the complete amino acid sequence of the Phl p 4 molecule can be constructed from the first 33 amino acid positions, determined by protein sequencing, and the deduced amino acid sequence (477 positions), which can be derived from the clones prepared with primers No. 29/No. 85 and No. 82/anchor primer. The two clones overlap in 197 positions of their nucleotide sequence. The peptide encoded by clone No. 29/No. 85 overlaps in 10 amino acid positions with the N-terminal sequence (positions 1-33), determined by direct amino acid sequencing, of Phl p 4, where the amino acids determined by the two methods correspond.

The amino acid sequence of Phl p 4 based on the directly determined N-terminal amino acids and the deduced amino acid sequence corresponds to the sequences listed in the sequence protocol under SEQ ID NO 2, 4 and 6.

PCR products were prepared with the specific sense primer No. 88 (Table 2) and the specific antisense primer No. 86 both using genomic and using cDNA from *Phleum pratense* and sequenced directly.

This enables PCR errors to be excluded and genetic variations (single nucleotide polymorphisms) to be discovered.

The single nucleotide polymorphisms found for the DNA sequence SEQ ID NO 1 are shown in Table 3. Some of these single nucleotide polymorphisms result in modified amino acids. These are shown in Table 4. Furthermore, DNA clones which result in deviating amino acids with respect to the dominant sequences SEQ ID NO 2, 4 and 6 were sequenced (Table 5). These amino acid variations are to be regarded as isoforms of the Phl p 4 molecule. The existence of such isoforms to be be expected owing to the heterogeneous isoelectric behaviour of natural Phl p 4. All pollen allergens known hitherto have such isoforms. The fact that the DNA fragment determined with primers No. 29 and 86 actually encodes for a protein which is identical with the natural Phl p 4 allergen can also be demonstrated, inter alia, by the fact that homologous peptide sequences in the deduced amino acid sequence of the recombinant Phl p 4 molecule according to the invention are found (FIG. 3) for the identified internal peptides P3, P4 and P5 (Table 1) of natural Phl p 4. The Phl p 4 amino acid sequence described shows that it is a basic molecule having a calculated isoelectric point of 8.99 (SEQ ID NO 2), 8.80 (SEQ ID NO 4) or 9.17 (SEQ ID NO 6), consisting of 500 amino acids. The quantitative amino acid composition is shown in Table 6. The calculated molecular weight of recombinant Phl p 4 is 55.762 (SEQ ID NO 2), 55.734 (SEQ ID NO 4) or 55.624 (SEQ ID NO 6) daltons.

This calculated molecular weight agrees very well with the molecular weight of natural Phl p 4 of 55 kDa determined by SDS-PAGE (Fahlbusch et al., 1998, Clin. Exp. Allergy 28: 799-807 and Suck et al., 2000, Clin. Exp. Allergy 30: 1395-1402).

Molecular weights of between 50 and 60 kDa have also been described for the group 4 allergens of related grass species (Su et al., 1991, Clin. Exp. Allergy 21: 449-455; Jaggi et al., 1989, Int. Arch. Allergy Appl. Immunol. 89: 342-348; Jaggi et al., 1989, J. Allergy Clin. Immunol. 83: 845-852; Leduc-Brodard et al., 1996, J. Allergy Clin. Immunol. 98: 1065-1072; 14-17).

For the preparation of the recombinant Phl p 4 protein, the DNA sequence according to SEQ ID NO 1, 3 and/or 5 encoding for Phl p 4 was inserted into expression vectors (for example pProEx, pλCro, pSE 380). For the N-terminal amino acids known from protein sequencing, *E. coli* optimised codons were used.

After transformation into *E. coli*, expression and purification of the recombinant Phl p 4 by various separation methods, the resultant protein was subjected to a refolding process.

This rPhl p 4 protein obtained in this way gives a single band in the SDS-PAGE which covers the same molecular weight range as natural Phl p 4. The immunological reactivity of rPhl p 4 has been demonstrated by reaction with the murine monoclonal antibodies 5H1 and 3C4, which had been induced using natural Phl p 4 and cross-react with the homologous proteins (group 4) of the *Poaceae* (Fahlbusch et al., 1998, Clin. Exp. Allergy 28:799-807; Gavrović-Jankulović et al., 2000, Invest. Allergol. Clin. Immunol. 10 (6): 361-367) (FIG. 4). rPhl p 4 reacts with IgE antibodies of allergy sufferers which have demonstrated IgE reactivity with natural Phl p 4. This IgE reactivity and thus the action as allergen has been demonstrated both in the dot test, Western blot and also after adsorption of the allergen on polystyrene microtitre plates. Detection by Western blot is shown in FIG. 5. On reaction of rPhl p 4 with basophiles of allergen group 4-reactive grass pollen allergy sufferers, these are stimulated to increased expression of the activation marker CD 203c. This basophile activation by rPhl p 4 clearly shows that this molecule also acts functionally as an allergen.

This rPhl p 4 allergen can thus be employed for the highly specific diagnosis of grass pollen allergy sufferers. This diagnosis can be carried out in vitro by detection of specific antibodies (IgE, IgG1-4, IgA) and reaction with IgE-loaded effector cells (for example basophiles from the blood) or in vivo by skin test reactions and provocation at the reaction organ.

The reaction of rPhl p 4 with T-lymphocytes of grass pollen allergy sufferers has been detected by allergen-specific stimulation of the T-lymphocytes for proliferation and cytokine synthesis both with T-cells in freshly prepared blood lymphocytes and on established nPhl p 4-reactive T-cell lines and clones.

Based on the rPhl p 4 DNA sequence described, partial sequences encoding for peptides having from 50 to 350 amino acids were cloned into expression vectors. These partial sequences cover sequentially the complete sequence of rPhl p 4, with overlaps of at least 12 amino acids occurring. The expressed peptides correspond to Phl p 4 fragments. These Phl p 4 fragments do not react individually or as a mixture with the IgE antibodies of allergy sufferers or only do so to a small extent, so that they can be classified as hypoallergenic. In contrast, the mixture of these fragments is capable, in the same way as complete recombinant or natural Phl p 4, of stimulating T-lymphocytes of grass pollen allergy sufferers having Phl p 4 reactivity.

FIG. 4 shows as an example the characterisation of two such Phl p 4 fragments corresponding to amino acids 1-200 and 185-500 by binding to Phl p 4-specific monoclonal mouse antibodies. The C-terminal fragment 185-500 reacts only with monoclonal antibody 5H1, while the N-terminal fragment 1-200 clearly reacts with monoclonal antibody 3C4. It can be seen from FIG. 5 that fragment 185-500 reacts less strongly with the IgE from the sera of allergy sufferers B and C, i.e. is less allergenic than fragment 1-200, which has reduced IgE reactivity (hypoallergeneity), at least to patient serum C.

The present invention therefore also relates to a DNA molecule described above or below, encoding for a fragment 1-200, with amino acids 1-200 of Phl p 4, and a DNA molecule encoding for a fragment 285-500, with amino acids 285-500 of Phl p 4.

The triplets encoding for the cysteines were modified by site-specific mutagenesis in such a way that they encode for other amino acids, preferably serine. Both variants in which individual cysteines have been replaced and those in which various combinations of 2 cysteine radicals or all 5 cysteines have been modified have been prepared. The expressed proteins of these cysteine point mutants have highly reduced or zero reactivity with IgE antibodies of allergy sufferers, but react with the T-lymphocytes of these patients. The present invention therefore furthermore relates to a DNA molecule described above or below in which one, more or all of the cysteine radicals of the corresponding polypeptide have been replaced by another amino acid by site-specific mutagenesis.

The immunomodulatory activity of the hypoallergenic fragments which correspond to polypeptides having T-cell epitopes and those of the hypoallergenic point mutants (for example cysteine polymorphisms) has been demonstrated by reaction thereof with T-cells of grass pollen allergy sufferers.

Such hypoallergenic fragments or point mutants of the cysteines can be employed as preparations for the hyposensitisation of allergy sufferers since they react with equal effectiveness with the T-cells, but, owing to the reduced or entirely absent IgE reactivity, result in reduced IgE-mediated side effects.

If the nucleic acids encoding for the hypoallergenic Phl p 4 variants or the unmodified DNA encoding for Phl p 4 are ligated with a human expression vector, these constructs can likewise be used as preparations for immuno-therapy (DNA vaccination).

Finally, the present invention relates to pharmaceutical compositions comprising at least one DNA molecule described above or at least one expression vector described above and optionally further active ingredients and/or adjuvants for immunotherapeutic DNA vaccination of patients having allergies in the triggering of which group 4 allergens of the *Poaceae* are involved and/or for the prevention of such allergies.

A further group of pharmaceutical compositions according to the invention comprises, instead of the DNA, at least one polypeptide described above and is suitable for the diagnosis and/or treatment of the said allergies.

Pharmaceutical compositions in the sense of the present invention comprise, as active ingredients, a polypeptide according to the invention or an expression vector and/or respective pharmaceutically usable derivatives thereof, including mixtures thereof in all ratios. The active ingredients according to the invention can be brought here into a suitable dosage form together with at least one solid, liquid and/or semi-liquid excipient or adjuvant and optionally in combination with one or more further active ingredients.

Particularly suitable adjuvants are immunostimulatory DNA or oligonucleotides having CpG motives.

These compositions can be used as therapeutic agents or diagnostic agents in human or veterinary medicine. Suitable excipients are organic or inorganic substances which are suitable for parenteral administration and do not adversely affect the action of the active ingredient according to the invention. Particularly suitable for parenteral administration are solutions, preferably oil-based or aqueous solutions, furthermore suspensions, emulsions or implants. The active ingredient according to the invention may also be lyophilised and the resultant lyophilisates used, for example, for the preparation of injection preparations. The compositions indicated may be sterilised and/or comprise adjuvants, such as lubricants, preservatives, stabilisers and/or wetting agents, emulsifiers, salts for modifying the osmotic pressure, buffer substances and/or a plurality of further active ingredients.

Furthermore, sustained-release preparations can be obtained by corresponding formulation of the active ingredient according to the invention.

The invention thus also serves for improving in vitro diagnosis as part of allergen component-triggering identification of the patient-specific sensitisation spectrum. The invention likewise serves for the preparation of significantly improved preparations for the specific immunotherapy of grass pollen allergies.

TABLE 1

Amino acid sequence of Phl p 4 peptides

| Preparation | Peptide batch | SEQ ID NO | 1 | 6 | 11 | 16 | 21 | 26 | 31 |
|---|---|---|---|---|---|---|---|---|---|
| Intact Phl p 4 | P1-a | 35 | YFPP'P' | AAKED | FLGXL | VKEIP | PRLLY | AKSSP | AYP |
| | P1-b | 36 | YFPP'P' | AAKED | FLGXL | VKE-P | PRLLY | AKSSP | |
| | P1-c | 37 | YFPXX | AAKED | FLGXL | | | | |
| | P1-d | 38 | YFPXX | AKKED | FLGXL | | | | |
| | P1-e | 39 | YFPXX | AAKDD | FLGXL | | | | |
| | P1-f | 40 | YFPXX | LANED | F | | | | |
| Glu-C fragments | P2 | 41 | SATPF | XHRKG | VLFNI | QYV | | | |
| | P3 | 42 | GLXYR | XLXPE | | | | | |
| Lys-C fragments | P4 | 43 | KXMGD | DHFXA | VR | | | | |
| | P5 | 44 | APEGA | VDI I | | | | | |
| CNBr fragment | P6 | 45 | MEPYV | SINPV | QAYAN | Y | | | |

TABLE 2

Degenerated and specific sense and antisense primers constructed on the basis of Phl p 4 peptide sequences and DNA sequences

| Primer No. | Peptide/ DNA | Sense/ anti-sense | SEQ ID NO | Nucleotide sequence |
|---|---|---|---|---|
| 29 | Phl p 4-P1 | s | 46 | YTN TAY GCN AAR WSN WSN CCN GCN TAY CC |
| 30 | Phl p 4-P2 | s | 47 | CAY MGN AAR GGN GTN YTN TTY AAY ATM C |
| 37 | Phl p 4-P6 | as | 48 | TAR TTN GCR TAN GCY TGN ACN GGR TT |
| 82 | Phl p 4-DNA-NYW | s | 49 | ACT ACT GGT TCG CCC CGG GAG CC |
| 85 | Phl p 4-DNA-GLV | as | 50 | TGA AGT ATT TCT GGC CCC ACA CCA AAC C |
| 86 | Phl p 4-DNA-QRL | as | 51 | CCC TTG GTG ATG GCG AGC CTC TGG |
| 88 | Phl p 4-DNA-PSV | s | 52 | CTC AGT CCT GGG GCA GAC CAT CC |

The nucleotide sequences of primers 82, 85, 86 and 88 is shown in the usual 4-letter code. In the case of primers 29, 30 and 37, the IUPAC-IUB DNA code is used; the letter 'N' here stands for inosine.

TABLE 3

Detected single nucleotide polymorphisms

| Position in sequence | Nucleotide according to SEQ ID NO 1 | Detected SNPs |
|---|---|---|
| 85 | T | A |
| 130 | C | A |
| 159 | G | A |
| 160 | A | C |
| 169 | G | A |
| 185 | C | T |
| 186 | C | A |
| 222 | G | C |
| 226 | G | A |
| 227 | G | C |
| 228 | T | C |
| 237 | C | T |
| 273 | C | T |
| 285 | C | T |
| 286 | C | T |
| 298 | G | A |
| 299 | A | C |
| 303 | C | T |
| 309 | C | G |
| 318 | T | C |
| 320 | G | A |
| 333 | C | G |
| 348 | G | C |
| 369 | C | G |
| 409 | C | T |
| 411 | C | T |
| 420 | T | C |
| 421 | A | C |
| 423 | A | C |
| 424 | G | A |
| 425 | T | C |
| 456 | C | G |
| 462 | C | A |
| 522 | G | C |
| 525 | C | G |
| 567 | G | A |
| 618 | C | T |
| 655 | A | C |
| 657 | G | A |
| 662 | G | A |
| 680 | C | T |
| 684 | G | C |
| 690 | C | A |
| 691 | G | A |
| 693 | G | A |
| 703 | C | T, A |
| 710 | A | C |
| 711 | G | A |
| 713 | C | T |
| 743 | G | A |
| 750 | G | A |
| 768 | C | T |
| 773 | A | C |
| 790 | G | A |
| 798 | G | C |
| 801 | G | A |
| 804 | C | G |
| 809 | C | A |
| 834 | G | C |
| 844 | C | A |
| 859 | A | T |
| 865 | A | G |
| 879 | G | C |
| 895 | G | C |
| 900 | G | C, A |
| 918 | G | A |
| 961 | A | G |
| 962 | A | C |
| 964 | A | C |
| 987 | G | C |
| 994 | A | T |
| 1020 | G | A |
| 1023 | G | C |
| 1036 | G | C |
| 1040 | C | T |
| 1041 | G | C |
| 1047 | C | A |
| 1051 | A | G |
| 1052 | G | A, C |
| 1053 | G | A, C, T |
| 1056 | G | C |
| 1069 | T | C |
| 1073 | G | A |
| 1084 | C | G |
| 1086 | G | C |
| 1090 | C | T |
| 1098 | G | C |
| 1151 | G | C |
| 1152 | G | C |
| 1155 | G | C |
| 1161 | G | C |
| 1185 | C | G |
| 1229 | G | C |
| 1233 | G | C |
| 1239 | A | C |
| 1240 | T | C |
| 1242 | G | C |
| 1257 | G | C |
| 1266 | C | T |
| 1269 | C | T |
| 1278 | A | C, G |
| 1305 | C | G |
| 1308 | C | T |
| 1311 | C | A |
| 1335 | G | C |
| 1350 | G | C |
| 1357 | T | A |
| 1359 | A | G |
| 1370 | G | C |
| 1377 | T | C |
| 1378 | T | A |

TABLE 3-continued

Detected single nucleotide polymorphisms

| Position in sequence | Nucleotide according to SEQ ID NO 1 | Detected SNPs |
|---|---|---|
| 1379 | T | A |
| 1383 | G | C |
| 1398 | C | T |
| 1411 | T | C |
| 1414 | C | G |
| 1425 | C | A |
| 1428 | C | T |
| 1443 | G | C |
| 1449 | C | T |
| 1464 | G | A |
| 1485 | G | A |
| 1498 | A | C |

TABLE 4

Amino acid exchanges as a consequence of single nucleotide polymorphisms

| Position in sequence | Amino acid according to SEQ ID NO 2 | Detected exchanges |
|---|---|---|
| 6 | A | L |
| 7 | A | K |
| 8 | K | N |
| 9 | E | D |
| 29 | S | T |
| 54 | I | L |
| 57 | V | I |
| 62 | A | V |
| 76 | G | T, N, S |
| 100 | E | T |
| 107 | S | N |
| 137 | H | Y |
| 141 | T | P |
| 142 | V | A, T |
| 189 | T | K |
| 219 | K | Q |
| 221 | R | K |
| 227 | P | L |
| 231 | V | I |
| 235 | P | T, S |
| 237 | K | T |
| 238 | A | V |
| 248 | R | K |
| 258 | D | A |
| 264 | V | I |
| 270 | T | K |
| 282 | Q | K |
| 287 | M | L |
| 289 | S | G |
| 299 | A | P |
| 321 | N | A |
| 322 | I | L |
| 332 | T | S |
| 346 | E | Q |
| 347 | P | L |
| 351 | R | E, T |
| 357 | F | L |
| 358 | S | N |
| 362 | L | V |
| 364 | P | S |
| 384 | W | S |
| 410 | G | A |
| 419 | E | D |
| 456 | F | Y |
| 457 | S | A, N |
| 460 | L | K |
| 468 | K | M |
| 472 | Q | E |
| 498 | K | Q |

TABLE 5

Deviating amino acid positions in individual recombinant Phl p 4 clones compared with SEQ ID NO 2

| Example | Deviating positions* |
|---|---|
| Clone 1 | L54, I57, V62, S76, T100, N107, Y137, P141, T142, K189, Q219, K221, L227, I231, S235, T237, V238, K248, A258, I264, K270, K282, L287, P299, A321, L322, S332, Q346, P347, T351, L357, N358, V362, S384, A410, D419, Y456, A457, K460, E472 |
| Clone 2 | L54, I57, V62, T76, T100, N107, Y137, P141, T142, K189, Q219, K221, I231, S235, T237, V238, K248, A258, I264, K270, K282, L287, P299, A321, L322, S332, Q346, P347, T351, L357, N358, V362, S384, A410, D419, Y456, A457, K460, E472 |
| Clone 3 | P141, K282, L287, P299, L347, E351 |
| Clone 4 | G289, A410, D419, Y456, A457, K460, E472 |
| Clone 5 | L347, E351, S384, A410, D419, Y456, A457, K460, E472 |
| Clone 6 | N107, Y137, P141, T142, K189, Q219, K221, I231, S235, T237, V238, K248, A258, I264, K270, K282, L287, P299, A321, L322, S332, Q346, P347, T351, L357, N358, V362, S384, A410, D419, Y456, A457, K460 |
| Clone 7 | K248, A258, I264, K270, K282, L287, P299, A321, L322, S332, Q346, P347, T351, L357, N358, V362, S384 |
| Clone 8 | Q219, K221, I231, S235, T237, V238, K248, A258, I264, K270, K282, L287, P299, E351 |
| Clone 9 | M231, T246, A251, C263, G289, L307, L309, E334 |
| Clone 10 | Q219, K221, I231, S235, T237, M238, V242, V246, K248, A258, I264, K270, K282, L287, P299, A321, L322, S332, Q346, P347, T351, N358, V362, S384, insertion of GA between positions 407 and 408, N452, Y456, A457, K460, E472 |
| Clone 11 | Insertion of GA between positions 407 and 408 |

*[Amino acid according to SEQ ID NO 2/position in sequence/deviating amino acid]

TABLE 6

Amino acid composition of Phl p 4

| Amino acids | Number | % by weight |
|---|---|---|
| Charged | 138/138/138 | 33.89/33.86/33.93 |
| Acid | 45/46/43 | 9.82/10.05/9.38 |
| Basic | 54/53/55 | 13.67/13.39/13.78 |
| Polar | 120/119/124 | 24.88/24.71/25.89 |
| Hydrophobic | 180/180/180 | 35.64/35.66/35.43 |
| A Ala | 40/40/41 | 5.10/5.10/5.24 |
| C Cys | 5/5/5 | 0.92/0.93/0.93 |
| D Asp | 24/24/24 | 4.95/4.96/4.97 |
| E Glu | 21/22/19 | 4.86/5.10/4.41 |
| F Phe | 24/24/22 | 6.33/6.34/5.82 |
| G Gly | 42/42/40 | 4.30/4.30/4.10 |
| H His | 10/10/9 | 2.46/2.46/2.22 |
| I Ile | 29/29/30 | 5.88/5.89/6.10 |
| K Lys | 29/29/33 | 6.67/6.67/7.60 |
| L Leu | 33/33/35 | 6.70/6.70/7.12 |
| M Met | 11/11/10 | 2.59/2.59/2.36 |
| N Asn | 22/22/23 | 4.50/4.50/4.72 |
| P Pro* | 38/39/39 | 6.62/6.80/6.81 |
| Q Gln | 15/15/15 | 3.45/3.45/3.46 |
| R Arg | 25/24/22 | 7.00/6.73/6.18 |
| S Ser | 32/32/33 | 5.00/5.00/5.17 |
| T Thr | 22/21/22 | 3.99/3.81/4.00 |
| V Val | 41/41/40 | 7.29/7.29/7.13 |
| W Trp | 13/13/12 | 4.34/4.34/4.02 |
| Y Tyr | 24/24/26 | 7.02/7.03/7.63 |

*including hydroxyproline

The values are given for the three dominant sequences in the order SEQ ID NO2/SEQ ID NO 4/SEQ ID NO 6.

We claim:

1. An isolated polypeptide which is
   (a) a polypeptide which consists of the polypeptide sequence set forth in SEQ ID NO: 2, SEQ ID NO: 4 or SEQ ID NO: 6,
   (b) a polypeptide consisting of the polypeptide sequence which is encoded by the polynucleotide sequence set forth in SEQ ID NO: 1, SEQ ID NO: 3 or SEQ ID NO: 5, or
   (c) a polypeptide variant consisting of the polypeptide sequence set forth in SEQ ID NO: 2 with the amino acid variations set forth in clones 1 to 11, wherein
   (1) clone 1 consists of L54, I57, V62, S76, T100, N107, Y137, P141, T142, K189, Q219, K221, L227, I231, S235, T237, V238, K248, A258, I264, K270, K282, L287, P299, A321, L322, S332, Q346, P347, T351, L357, N358, V362, S384, A410, D419, Y456, A457, K460, and E472;
   (2) clone 2 consists of L54, I57, V62, T76, T100, N107, Y137, P141, T142, K189, Q219, K221, I231, S235, T237, V238, K248, A258, I264, K270, K282, L287, P299, A321, L322, S332, Q346, P347, T351, L357, N358, V362, S384, A410, D419, Y456, A457, K460, and E472;
   (3) clone 3 consists of P141, K282, L287, P299, L347, and E351;
   (4) clone 4 consists of G289, A410, D419, Y456, A457, K460, and E472;
   (5) clone 5 consists of L347, E351, S384, A410, D419, Y456, A457, K460, and E472;
   (6) clone 6 consists of N107, Y137, P141, T142, K189, Q219, K221, I231, S235, T237, V238, K248, A258, I264, K270, K282, L287, P299, A321, L322, S332, Q346, P347, T351, L357, N358, V362, S384, A410, D419, Y456, A457, and K460;
   (7) clone 7 consists of K248, A258, I264, K270, K282, L287, P299, A321, L322, S332, Q346, P347, T351, L357, N358, V362, and S384;
   (8) clone 8 consists of Q219, K221, I231, S235, T237, V238, K248, A258, I264, K270, K282, L287, P299, and E351;
   (9) clone 9 consists of M231, T246, A251, C263, G289, L307, L309, and E334;
   (10) clone 10 consists of Q219, K221, I231, S235, T237, M238, V242, V246, K248, A258, I264, K270, K282, L287, P299, A321, L322, S332, Q346, P347, T351, N358, V362, S384, insertion of GA between positions 407 and 408, N452, Y456, A457, K460, and E472;
   (11) clone 11 consists of insertion of GA between positions 407 and 408.

2. A pharmaceutical composition comprising at least one polypeptide according to claim 1 and a pharmaceutically acceptable carrier.

3. An isolated polypeptide according to claim 1 wherein each of the polypeptides of (a) to (c) is immunogenic and induces an immunomodulatory T-cell reactive response in a host.

4. An isolated polypeptide which comprises (a) a polypeptide which is encoded by a single nucleotide polymorph of the polynucleotide sequence set forth in SEQ ID NO: 1, or (b) a single amino acid polymorph of the polypeptide sequence set forth in SEQ ID NO: 2.

5. The isolated polypeptide according to claim 1, which is a recombinant polypeptide.

6. A polypeptide fragment which is
   (a) a polypeptide consisting of amino acids 1-200 of the polypeptide sequence set forth in SEQ ID NO: 2, SEQ ID NO: 4, SEQ ID NO: 6 or a polypeptide variant consisting of the polypeptide sequence set forth in SEQ ID NO: 2 with the amino acid variations set forth in clones 1 to 11, wherein
   (1) clone 1 consists of L54, I57, V62, S76, T100, N107, Y137, P141, T142, K189, Q219, K221, L227, I231, S235, T237, V238, K248, A258, I264, K270, K282, L287, P299, A321, L322, S332, Q346, P347, T351, L357, N358, V362, S384, A410, D419, Y456, A457, K460, and E472;
   (2) clone 2 consists of L54, I57, V62, T76, T100, N107, Y137, P141, T142, K189, Q219, K221, I231, S235, T237, V238, K248, A258, I264, K270, K282, L287, P299, A321, L322, S332, Q346, P347, T351, L357, N358, V362, S384, A410, D419, Y456, A457, K460, and E472;
   (3) clone 3 consists of P141, K282, L287, P299, L347, and E351;
   (4) clone 4 consists of G289, A410, D419, Y456, A457, K460, and E472;

(5) clone 5 consists of L347, E351, S384, A410, D419, Y456, A457, K460, and E472;
(6) clone 6 consists of N107, Y137, P141, T142, K189, Q219, K221, I231, S235, T237, V238, K248, A258, I264, K270, K282, L287, P299, A321, L322, S332, Q346, P347, T351, L357, N358, V362, S384, A410, D419, Y456, A457, and K460;
(7) clone 7 consists of K248, A258, I264, K270, K282, L287, P299, A321, L322, S332, Q346, P347, T351, L357, N358, V362, and S384;
(8) clone 8 consists of Q219, K221, I231, S235, T237, V238, K248, A258, I264, K270, K282, L287, P299, and E351;
(9) clone 9 consists of M231, T246, A251, C263, G289, L307, L309, and E334;
(10) clone 10 consists of Q219, K221, I231, S235, T237, M238, V242, V246, K248, A258, I264, K270, K282, L287, P299, A321, L322, S332, Q346, P347, T351, N358, V362, S384, insertion of GA between positions 407 and 408, N452, Y456, A457, K460, and E472;
(11) clone 11 consists of insertion of GA between positions 407 and 408; or
(b) a polypeptide consisting of amino acids 185-500 of the polypeptide sequence set forth in SEQ ID NO: 2, SEQ ID NO: 4, SEQ ID NO: 6 or a polypeptide variant consisting of the polypeptide sequence set forth in SEQ ID NO: 2 comprising with the amino acid variations set forth in clones 1 to 11, wherein
(1) clone 1 consists of L54, I57, V62, S76, T100, N107, Y137, P141, T142, K189, Q219, K221, L227, I231, S235, T237, V238, K248, A258, I264, K270, K282, L287, P299, A321, L322, S332, Q346, P347, T351, L357, N358, V362, S384, A410, D419, Y456, A457, K460, and E472;
(2) clone 2 comprises consists of L54, I57, V62, T76, T100, N107, Y137, P141, T142, K189, Q219, K221, I231, S235, T237, V238, K248, A258, I264, K270, K282, L287, P299, A321, L322, S332, Q346, P347, T351, L357, N358, V362, S384, A410, D419, Y456, A457, K460, and E472;
(3) clone 3 consists of P141, K282, L287, P299, L347, and E351;
(4) clone 4 consists of G289, A410, D419, Y456, A457, K460, and E472;
(5) clone 5 consists of L347, E351, S384, A410, D419, Y456, A457, K460, and E472;
(6) clone 6 consists of N107, Y137, P141, T142, K189, Q219, K221, I231, S235, T237, V238, K248, A258, I264, K270, K282, L287, P299, A321, L322, S332, Q346, P347, T351, L357, N358, V362, S384, A410, D419, Y456, A457, and K460;
(7) clone 7 consists of K248, A258, I264, K270, K282, L287, P299, A321, L322, S332, Q346, P347, T351, L357, N358, V362, and S384;
(8) clone 8 consists of Q219, K221, I231, S235, T237, V238, K248, A258, I264, K270, K282, L287, P299, and E351;
(9) clone 9 consists of M231, T246, A251, C263, G289, L307, L309, and E334;
(10) clone 10 consists of Q219, K221, I231, S235, T237, M238, V242, V246, K248, A258, I264, K270, K282, L287, P299, A321, L322, S332, Q346, P347, T351, N358, V362, S384, insertion of GA between positions 407 and 408, N452, Y456, A457, K460, and E472;
(11) clone 11 consists of insertion of GA between positions 407 and 408.

* * * * *

UNITED STATES PATENT AND TRADEMARK OFFICE
CERTIFICATE OF CORRECTION

PATENT NO.      : 8,128,935 B2
APPLICATION NO. : 10/518927
DATED           : March 6, 2012
INVENTOR(S)     : Helmut Fiebig et al.

It is certified that error appears in the above-identified patent and that said Letters Patent is hereby corrected as shown below:

Column 51, line 27 reads: "NO: 2 comprising with the amino acid variations set" should read --NO: 2 with the amino acid variations set--.

Column 52, line 1 reads: "(2) clone 2 comprises consists of L54, I57, V62, T76," should read --(2) clone 2 consists of L54, I57, V62, T76,--.

Signed and Sealed this
Fifth Day of June, 2012

David J. Kappos
*Director of the United States Patent and Trademark Office*

SEQUENCE LISTING

<160> NUMBER OF SEQ ID NOS: 52

<210> SEQ ID NO 1
<211> LENGTH: 1503
<212> TYPE: DNA
<213> ORGANISM: Phleum pratense
<220> FEATURE:
<221> NAME/KEY: artificial_DNA_sequence
<222> LOCATION: (1)..(69)
<223> OTHER INFORMATION: DNA sequence derived from sequenced protein
<220> FEATURE:
<221> NAME/KEY: native_DNA_sequence
<222> LOCATION: (70)..(1503)
<223> OTHER INFORMATION:
<220> FEATURE:
<221> NAME/KEY: CDS
<222> LOCATION: (1)..(1503)
<223> OTHER INFORMATION:

<400> SEQUENCE: 1

```
tac ttc ccg ccg ccg gct gct aaa gaa gac ttc ctg ggt tgc ctg gtt        48
Tyr Phe Pro Pro Pro Ala Ala Lys Glu Asp Phe Leu Gly Cys Leu Val
1               5                   10                  15 aaa gaa atc ccg ccg cgt ctg ttg tac gcg aaa tcg tcg ccg gcg tat        96
Lys Glu Ile Pro Pro Arg Leu Leu Tyr Ala Lys Ser Ser Pro Ala Tyr
            20                  25                  30 ccc tca gtc ctg ggg cag acc atc cgg aac tcg cgg tgg tcg tcg ccg       144
Pro Ser Val Leu Gly Gln Thr Ile Arg Asn Ser Arg Trp Ser Ser Pro
        35                  40                  45 gac aac gtg aag ccg atc tac atc gtc acc ccc acc aac gcc tcc cac       192
Asp Asn Val Lys Pro Ile Tyr Ile Val Thr Pro Thr Asn Ala Ser His
    50                  55                  60 atc cag tcc gcc gtg gtg tgc ggc cgc cgg cac ggt gtc cgc atc cgc       240
Ile Gln Ser Ala Val Val Cys Gly Arg Arg His Gly Val Arg Ile Arg
65                  70                  75                  80 gtg cgc agc ggc ggg cac gac tac gag ggc ctc tcg tac cgg tcc ctg       288
Val Arg Ser Gly Gly His Asp Tyr Glu Gly Leu Ser Tyr Arg Ser Leu
                85                  90                  95 cag ccc gag gag ttc gcc gtc gtc gac ctt agc aag atg cgg gcc gtg       336
Gln Pro Glu Glu Phe Ala Val Val Asp Leu Ser Lys Met Arg Ala Val
            100                 105                 110 tgg gtg gac ggg aag gcc cgc acg gcg tgg gtc gac tcc ggc gcg cag       384
Trp Val Asp Gly Lys Ala Arg Thr Ala Trp Val Asp Ser Gly Ala Gln
        115                 120                 125 ctc ggc gag ctc tac tac gcc atc cac aag gcg agt aca gtg ctg gcg       432
Leu Gly Glu Leu Tyr Tyr Ala Ile His Lys Ala Ser Thr Val Leu Ala
    130                 135                 140 ttc ccg gcc ggc gtg tgc ccg acc atc ggc gtg ggc ggc aac ttc gcg       480
Phe Pro Ala Gly Val Cys Pro Thr Ile Gly Val Gly Gly Asn Phe Ala
145                 150                 155                 160 ggc ggc ggc ttc ggc atg ctg ctg cgc aag tac ggc atc gcg gcc gag       528
Gly Gly Gly Phe Gly Met Leu Leu Arg Lys Tyr Gly Ile Ala Ala Glu
                165                 170                 175 aac gtc atc gac gtg aag ctc gtc gac gcc aac ggc acg ctg cac gac       576
Asn Val Ile Asp Val Lys Leu Val Asp Ala Asn Gly Thr Leu His Asp
            180                 185                 190 aag aag tcc atg ggc gac gac cat ttc tgg gcc gtc agg ggc ggc ggg       624
Lys Lys Ser Met Gly Asp Asp His Phe Trp Ala Val Arg Gly Gly Gly
        195                 200                 205 ggc gag agc ttc ggc atc gtg gtc gcg tgg aag gtg agg ctc ctg ccg       672
```

```
Gly Glu Ser Phe Gly Ile Val Val Ala Trp Lys Val Arg Leu Leu Pro
    210                 215                 220 gtg ccg ccc acg gtg acc gtg ttc aag atc ccc aag aag gcg agc gag       720
Val Pro Pro Thr Val Thr Val Phe Lys Ile Pro Lys Lys Ala Ser Glu
225                 230                 235                 240 ggc gcc gtg gac atc atc aac agg tgg cag gtg gtc gcg ccg cag ctc       768
Gly Ala Val Asp Ile Ile Asn Arg Trp Gln Val Val Ala Pro Gln Leu
                245                 250                 255 ccc gac gac ctc atg atc cgc gtc atc gcg cag ggc ccc acg gcc acg       816
Pro Asp Asp Leu Met Ile Arg Val Ile Ala Gln Gly Pro Thr Ala Thr
            260                 265                 270 ttc gag gcc atg tac ctg ggc acc tgc caa acc ctg acg ccg atg atg       864
Phe Glu Ala Met Tyr Leu Gly Thr Cys Gln Thr Leu Thr Pro Met Met
        275                 280                 285 agc agc aag ttc ccg gag ctc ggc atg aac gcc tcg cac tgc aac gag       912
Ser Ser Lys Phe Pro Glu Leu Gly Met Asn Ala Ser His Cys Asn Glu
    290                 295                 300 atg tcg tgg atc cag tcc atc ccc ttc gtc cac ctc ggc cac agg gac       960
Met Ser Trp Ile Gln Ser Ile Pro Phe Val His Leu Gly His Arg Asp
305                 310                 315                 320 aac atc gag gac gac ctc ctc aac cgg aac aac acc ttc aag ccc ttc      1008
Asn Ile Glu Asp Asp Leu Leu Asn Arg Asn Asn Thr Phe Lys Pro Phe
                325                 330                 335 gcc gaa tac aag tcg gac tac gtc tac gag ccg ttc ccc aag agg gtg      1056
Ala Glu Tyr Lys Ser Asp Tyr Val Tyr Glu Pro Phe Pro Lys Arg Val
            340                 345                 350 tgg gag cag atc ttc agc acc tgg ctc ctg aag ccc ggc gcg ggg atc      1104
Trp Glu Gln Ile Phe Ser Thr Trp Leu Leu Lys Pro Gly Ala Gly Ile
        355                 360                 365 atg atc ttc gac ccc tac ggc gcc acc atc agc gcc acc ccg gag tgg      1152
Met Ile Phe Asp Pro Tyr Gly Ala Thr Ile Ser Ala Thr Pro Glu Trp
    370                 375                 380 gcg acg ccg ttc cct cac cgc aag ggc gtc ctc ttc aac atc cag tac      1200
Ala Thr Pro Phe Pro His Arg Lys Gly Val Leu Phe Asn Ile Gln Tyr
385                 390                 395                 400 gtc aac tac tgg ttc gcc ccg gga gcc ggc gcg gcg cca ttg tcg tgg      1248
Val Asn Tyr Trp Phe Ala Pro Gly Ala Gly Ala Ala Pro Leu Ser Trp
                405                 410                 415 agc aag gag atc tac aac tac atg gag cca tac gtg agc aag aac ccc      1296
Ser Lys Glu Ile Tyr Asn Tyr Met Glu Pro Tyr Val Ser Lys Asn Pro
            420                 425                 430 agg cag gcc tac gcc aac tac agg gac atc gac ctc ggg agg aac gag      1344
Arg Gln Ala Tyr Ala Asn Tyr Arg Asp Ile Asp Leu Gly Arg Asn Glu
        435                 440                 445 gtg gtg aac gac gtc tcc acc ttc agc agc ggt ttg gtg tgg ggc cag      1392
Val Val Asn Asp Val Ser Thr Phe Ser Ser Gly Leu Val Trp Gly Gln
    450                 455                 460 aaa tac ttc aag ggc aat ttc cag agg ctc gcc atc acc aag ggc aag      1440
Lys Tyr Phe Lys Gly Asn Phe Gln Arg Leu Ala Ile Thr Lys Gly Lys
465                 470                 475                 480 gtg gat ccc acc gac tac ttc agg aac gag cag agc atc ccg ccg ctc      1488
Val Asp Pro Thr Asp Tyr Phe Arg Asn Glu Gln Ser Ile Pro Pro Leu
                485                 490                 495 atc aaa aag tac tga                                                  1503
Ile Lys Lys Tyr
            500

<210> SEQ ID NO 2
<211> LENGTH: 500
<212> TYPE: PRT
<213> ORGANISM: Phleum pratense
```

<400> SEQUENCE: 2

```
Tyr Phe Pro Pro Pro Ala Ala Lys Glu Asp Phe Leu Gly Cys Leu Val
1               5                   10                  15

Lys Glu Ile Pro Pro Arg Leu Leu Tyr Ala Lys Ser Ser Pro Ala Tyr
            20                  25                  30

Pro Ser Val Leu Gly Gln Thr Ile Arg Asn Ser Arg Trp Ser Ser Pro
        35                  40                  45

Asp Asn Val Lys Pro Ile Tyr Ile Val Thr Pro Thr Asn Ala Ser His
    50                  55                  60

Ile Gln Ser Ala Val Val Cys Gly Arg Arg His Gly Val Arg Ile Arg
65                  70                  75                  80

Val Arg Ser Gly Gly His Asp Tyr Glu Gly Leu Ser Tyr Arg Ser Leu
                85                  90                  95

Gln Pro Glu Glu Phe Ala Val Val Asp Leu Ser Lys Met Arg Ala Val
            100                 105                 110

Trp Val Asp Gly Lys Ala Arg Thr Ala Trp Val Asp Ser Gly Ala Gln
        115                 120                 125

Leu Gly Glu Leu Tyr Tyr Ala Ile His Lys Ala Ser Thr Val Leu Ala
130                 135                 140

Phe Pro Ala Gly Val Cys Pro Thr Ile Gly Val Gly Gly Asn Phe Ala
145                 150                 155                 160

Gly Gly Gly Phe Gly Met Leu Leu Arg Lys Tyr Gly Ile Ala Ala Glu
                165                 170                 175

Asn Val Ile Asp Val Lys Leu Val Asp Ala Asn Gly Thr Leu His Asp
            180                 185                 190

Lys Lys Ser Met Gly Asp Asp His Phe Trp Ala Val Arg Gly Gly Gly
        195                 200                 205

Gly Glu Ser Phe Gly Ile Val Val Ala Trp Lys Val Arg Leu Leu Pro
    210                 215                 220

Val Pro Pro Thr Val Thr Val Phe Lys Ile Pro Lys Lys Ala Ser Glu
225                 230                 235                 240

Gly Ala Val Asp Ile Ile Asn Arg Trp Gln Val Val Ala Pro Gln Leu
                245                 250                 255

Pro Asp Asp Leu Met Ile Arg Val Ile Ala Gln Gly Pro Thr Ala Thr
            260                 265                 270

Phe Glu Ala Met Tyr Leu Gly Thr Cys Gln Thr Leu Thr Pro Met Met
        275                 280                 285

Ser Ser Lys Phe Pro Glu Leu Gly Met Asn Ala Ser His Cys Asn Glu
    290                 295                 300

Met Ser Trp Ile Gln Ser Ile Pro Phe Val His Leu Gly His Arg Asp
305                 310                 315                 320

Asn Ile Glu Asp Asp Leu Leu Asn Arg Asn Asn Thr Phe Lys Pro Phe
                325                 330                 335

Ala Glu Tyr Lys Ser Asp Tyr Val Tyr Glu Pro Phe Pro Lys Arg Val
            340                 345                 350

Trp Glu Gln Ile Phe Ser Thr Trp Leu Leu Lys Pro Gly Ala Gly Ile
        355                 360                 365

Met Ile Phe Asp Pro Tyr Gly Ala Thr Ile Ser Ala Thr Pro Glu Trp
    370                 375                 380

Ala Thr Pro Phe Pro His Arg Lys Gly Val Leu Phe Asn Ile Gln Tyr
385                 390                 395                 400

Val Asn Tyr Trp Phe Ala Pro Gly Ala Gly Ala Ala Pro Leu Ser Trp
                405                 410                 415
```

```
Ser Lys Glu Ile Tyr Asn Tyr Met Glu Pro Tyr Val Ser Lys Asn Pro
        420                 425                 430

Arg Gln Ala Tyr Ala Asn Tyr Arg Asp Ile Asp Leu Gly Arg Asn Glu
            435                 440                 445

Val Val Asn Asp Val Ser Thr Phe Ser Ser Gly Leu Val Trp Gly Gln
    450                 455                 460

Lys Tyr Phe Lys Gly Asn Phe Gln Arg Leu Ala Ile Thr Lys Gly Lys
465                 470                 475                 480

Val Asp Pro Thr Asp Tyr Phe Arg Asn Glu Gln Ser Ile Pro Pro Leu
                485                 490                 495

Ile Lys Lys Tyr
            500

<210> SEQ ID NO 3
<211> LENGTH: 1503
<212> TYPE: DNA
<213> ORGANISM: Phleum pratense
<220> FEATURE:
<221> NAME/KEY: artificial_DNA_sequence
<222> LOCATION: (1)..(69)
<223> OTHER INFORMATION: DNA sequence derived from sequenced protein
<220> FEATURE:
<221> NAME/KEY: native_DNA_sequence
<222> LOCATION: (70)..(1503)
<223> OTHER INFORMATION:
<220> FEATURE:
<221> NAME/KEY: CDS
<222> LOCATION: (1)..(1503)
<223> OTHER INFORMATION:

<400> SEQUENCE: 3 tac ttc ccg ccg ccg gct gct aaa gaa gac ttc ctg ggt tgc ctg gtt      48
Tyr Phe Pro Pro Pro Ala Ala Lys Glu Asp Phe Leu Gly Cys Leu Val
1               5                   10                  15 aaa gaa atc ccg ccg cgt ctg ttg tac gcg aaa tcg tcg ccg gcg tat      96
Lys Glu Ile Pro Pro Arg Leu Leu Tyr Ala Lys Ser Ser Pro Ala Tyr
                20                  25                  30 ccc tca gtc ctg ggg cag acc atc cgg aac tcg cgg tgg tcg tcg ccg     144
Pro Ser Val Leu Gly Gln Thr Ile Arg Asn Ser Arg Trp Ser Ser Pro
            35                  40                  45 gac aac gtg aag ccg atc tac atc gtc acc ccc acc aac gcc tcc cac     192
Asp Asn Val Lys Pro Ile Tyr Ile Val Thr Pro Thr Asn Ala Ser His
        50                  55                  60 atc cag tcc gcc gtg gtg tgc ggc cgc cgg cac ggt gtc cgc atc cgc     240
Ile Gln Ser Ala Val Val Cys Gly Arg Arg His Gly Val Arg Ile Arg
65                  70                  75                  80 gtg cgc agc ggc ggg cac gac tac gag ggc ctc tcg tac cgg tcc ctg     288
Val Arg Ser Gly Gly His Asp Tyr Glu Gly Leu Ser Tyr Arg Ser Leu
                85                  90                  95 cag ccc gag gag ttc gcc gtc gtc gac ctt agc aag atg cgg gcc gtg     336
Gln Pro Glu Glu Phe Ala Val Val Asp Leu Ser Lys Met Arg Ala Val
                100                 105                 110 tgg gtg gac ggg aag gcc cgc acg gcg tgg gtc gac tcc ggc gcg cag     384
Trp Val Asp Gly Lys Ala Arg Thr Ala Trp Val Asp Ser Gly Ala Gln
            115                 120                 125 ctc ggc gag ctc tac tac gcc atc cac aag gcg agt cca gtg ctg gcg     432
Leu Gly Glu Leu Tyr Tyr Ala Ile His Lys Ala Ser Pro Val Leu Ala
        130                 135                 140 ttc ccg gcc ggc gtg tgc ccg acc atc ggc gtg ggc ggc aac ttc gcg     480
Phe Pro Ala Gly Val Cys Pro Thr Ile Gly Val Gly Gly Asn Phe Ala
145                 150                 155                 160 ggc ggc ggc ttc ggc atg ctg ctg cgc aag tac ggc atc gcg gcc gag     528
```

```
                                                         -continued

Gly Gly Gly Phe Gly Met Leu Leu Arg Lys Tyr Gly Ile Ala Ala Glu
                165                 170                 175 aac gtc atc gac gtg aag ctc gtc gac gcc aac ggc acg ctg cac gac       576
Asn Val Ile Asp Val Lys Leu Val Asp Ala Asn Gly Thr Leu His Asp
                180                 185                 190 aag aag tcc atg ggc gac gac cat ttc tgg gcc gtc agg ggc ggc ggg       624
Lys Lys Ser Met Gly Asp Asp His Phe Trp Ala Val Arg Gly Gly Gly
                195                 200                 205 ggc gag agc ttc ggc atc gtg gtc gcg tgg aag gtg agg ctc ctg ccg       672
Gly Glu Ser Phe Gly Ile Val Val Ala Trp Lys Val Arg Leu Leu Pro
        210                 215                 220 gtg ccg ccc acg gtg acc gtg ttc aag atc ccc aag aag gcg agc gag       720
Val Pro Pro Thr Val Thr Val Phe Lys Ile Pro Lys Lys Ala Ser Glu
225                 230                 235                 240 ggc gcc gtg gac atc atc aac agg tgg cag gtg gtc gcg ccg cag ctc       768
Gly Ala Val Asp Ile Ile Asn Arg Trp Gln Val Val Ala Pro Gln Leu
                245                 250                 255 ccc gac gac ctc atg atc cgc gtc atc gcg cag ggc ccc acg gcc acg       816
Pro Asp Asp Leu Met Ile Arg Val Ile Ala Gln Gly Pro Thr Ala Thr
                260                 265                 270 ttc gag gcc atg tac ctg ggc acc tgc caa acc ctg acg ccg atg atg       864
Phe Glu Ala Met Tyr Leu Gly Thr Cys Gln Thr Leu Thr Pro Met Met
                275                 280                 285 agc agc aag ttc ccc gag ctc ggc atg aac gcc tcg cac tgc aac gag       912
Ser Ser Lys Phe Pro Glu Leu Gly Met Asn Ala Ser His Cys Asn Glu
                290                 295                 300 atg tcg tgg atc cag tcc atc ccc ttc gtc cac ctc ggc cac agg gac       960
Met Ser Trp Ile Gln Ser Ile Pro Phe Val His Leu Gly His Arg Asp
305                 310                 315                 320 aac atc gag gac gac ctc ctc aac cgg aac aac acc ttc aag ccc ttc      1008
Asn Ile Glu Asp Asp Leu Leu Asn Arg Asn Asn Thr Phe Lys Pro Phe
                325                 330                 335 gcc gaa tac aag tcg gac tac gtc tac gag ccg ttc ccc aag gaa gtg      1056
Ala Glu Tyr Lys Ser Asp Tyr Val Tyr Glu Pro Phe Pro Lys Glu Val
                340                 345                 350 tgg gag cag atc ttc agc acc tgg ctc ctg aag ccc ggc gcg ggg atc      1104
Trp Glu Gln Ile Phe Ser Thr Trp Leu Leu Lys Pro Gly Ala Gly Ile
                355                 360                 365 atg atc ttc gac ccc tac ggc gcc acc atc agc gcc acc ccg gag tgg      1152
Met Ile Phe Asp Pro Tyr Gly Ala Thr Ile Ser Ala Thr Pro Glu Trp
        370                 375                 380 gcg acg ccg ttc cct cac cgc aag ggc gtc ctc ttc aac atc cag tac      1200
Ala Thr Pro Phe Pro His Arg Lys Gly Val Leu Phe Asn Ile Gln Tyr
385                 390                 395                 400 gtc aac tac tgg ttc gcc ccg gga gcc ggc gcg gcg cca ttg tcg tgg      1248
Val Asn Tyr Trp Phe Ala Pro Gly Ala Gly Ala Ala Pro Leu Ser Trp
                405                 410                 415 agc aag gag atc tac aac tac atg gag cca tac gtg agc aag aac ccc      1296
Ser Lys Glu Ile Tyr Asn Tyr Met Glu Pro Tyr Val Ser Lys Asn Pro
                420                 425                 430 agg cag gcc tac gcc aac tac agg gac atc gac ctc ggg agg aac gag      1344
Arg Gln Ala Tyr Ala Asn Tyr Arg Asp Ile Asp Leu Gly Arg Asn Glu
                435                 440                 445 gtg gtg aac gac gtc tcc acc ttc agc agc ggt ttg gtg tgg ggc cag      1392
Val Val Asn Asp Val Ser Thr Phe Ser Ser Gly Leu Val Trp Gly Gln
        450                 455                 460 aaa tac ttc aag ggc aat ttc cag agg ctc gcc atc acc aag ggc aag      1440
Lys Tyr Phe Lys Gly Asn Phe Gln Arg Leu Ala Ile Thr Lys Gly Lys
465                 470                 475                 480 gtg gat ccc acc gac tac ttc agg aac gag cag agc atc ccg ccg ctc      1488
```

```
Val Asp Pro Thr Asp Tyr Phe Arg Asn Glu Gln Ser Ile Pro Pro Leu
                485                 490                 495 atc aaa aag tac tga                                              1503
Ile Lys Lys Tyr
        500

<210> SEQ ID NO 4
<211> LENGTH: 500
<212> TYPE: PRT
<213> ORGANISM: Phleum pratense

<400> SEQUENCE: 4

Tyr Phe Pro Pro Ala Ala Lys Glu Asp Phe Leu Gly Cys Leu Val
1               5                   10                  15

Lys Glu Ile Pro Pro Arg Leu Leu Tyr Ala Lys Ser Ser Pro Ala Tyr
                20                  25                  30

Pro Ser Val Leu Gly Gln Thr Ile Arg Asn Ser Arg Trp Ser Ser Pro
            35                  40                  45

Asp Asn Val Lys Pro Ile Tyr Ile Val Thr Pro Thr Asn Ala Ser His
        50                  55                  60

Ile Gln Ser Ala Val Val Cys Gly Arg Arg His Gly Val Arg Ile Arg
65                  70                  75                  80

Val Arg Ser Gly Gly His Asp Tyr Glu Gly Leu Ser Tyr Arg Ser Leu
                85                  90                  95

Gln Pro Glu Glu Phe Ala Val Val Asp Leu Ser Lys Met Arg Ala Val
                100                 105                 110

Trp Val Asp Gly Lys Ala Arg Thr Ala Trp Val Asp Ser Gly Ala Gln
            115                 120                 125

Leu Gly Glu Leu Tyr Tyr Ala Ile His Lys Ala Ser Pro Val Leu Ala
130                 135                 140

Phe Pro Ala Gly Val Cys Pro Thr Ile Gly Val Gly Gly Asn Phe Ala
145                 150                 155                 160

Gly Gly Gly Phe Gly Met Leu Leu Arg Lys Tyr Gly Ile Ala Ala Glu
                165                 170                 175

Asn Val Ile Asp Val Lys Leu Val Asp Ala Asn Gly Thr Leu His Asp
            180                 185                 190

Lys Lys Ser Met Gly Asp Asp His Phe Trp Ala Val Arg Gly Gly Gly
        195                 200                 205

Gly Glu Ser Phe Gly Ile Val Val Ala Trp Lys Val Arg Leu Leu Pro
210                 215                 220

Val Pro Pro Thr Val Thr Val Phe Lys Ile Pro Lys Lys Ala Ser Glu
225                 230                 235                 240

Gly Ala Val Asp Ile Ile Asn Arg Trp Gln Val Val Ala Pro Gln Leu
                245                 250                 255

Pro Asp Asp Leu Met Ile Arg Val Ile Ala Gln Gly Pro Thr Ala Thr
            260                 265                 270

Phe Glu Ala Met Tyr Leu Gly Thr Cys Gln Thr Leu Thr Pro Met Met
        275                 280                 285

Ser Ser Lys Phe Pro Glu Leu Gly Met Asn Ala Ser His Cys Asn Glu
        290                 295                 300

Met Ser Trp Ile Gln Ser Ile Pro Phe Val His Leu Gly His Arg Asp
305                 310                 315                 320

Asn Ile Glu Asp Asp Leu Leu Asn Arg Asn Thr Phe Lys Pro Phe
                325                 330                 335

Ala Glu Tyr Lys Ser Asp Tyr Val Tyr Glu Pro Phe Pro Lys Glu Val
                340                 345                 350
```

```
Trp Glu Gln Ile Phe Ser Thr Trp Leu Leu Lys Pro Gly Ala Gly Ile
            355                 360                 365

Met Ile Phe Asp Pro Tyr Gly Ala Thr Ile Ser Ala Thr Pro Glu Trp
370                 375                 380

Ala Thr Pro Phe Pro His Arg Lys Gly Val Leu Phe Asn Ile Gln Tyr
385                 390                 395                 400

Val Asn Tyr Trp Phe Ala Pro Gly Ala Gly Ala Ala Pro Leu Ser Trp
                405                 410                 415

Ser Lys Glu Ile Tyr Asn Tyr Met Glu Pro Tyr Val Ser Lys Asn Pro
            420                 425                 430

Arg Gln Ala Tyr Ala Asn Tyr Arg Asp Ile Asp Leu Gly Arg Asn Glu
            435                 440                 445

Val Val Asn Asp Val Ser Thr Phe Ser Ser Gly Leu Val Trp Gly Gln
            450                 455                 460

Lys Tyr Phe Lys Gly Asn Phe Gln Arg Leu Ala Ile Thr Lys Gly Lys
465                 470                 475                 480

Val Asp Pro Thr Asp Tyr Phe Arg Asn Glu Gln Ser Ile Pro Pro Leu
                485                 490                 495

Ile Lys Lys Tyr
            500

<210> SEQ ID NO 5
<211> LENGTH: 1503
<212> TYPE: DNA
<213> ORGANISM: Phleum pratense
<220> FEATURE:
<221> NAME/KEY: artificial_DNA_sequence
<222> LOCATION: (1)..(69)
<223> OTHER INFORMATION: DNA sequence derived from sequenced protein
<220> FEATURE:
<221> NAME/KEY: native_DNA_sequence
<222> LOCATION: (70)..(1503)
<223> OTHER INFORMATION:
<220> FEATURE:
<221> NAME/KEY: CDS
<222> LOCATION: (1)..(1503)
<223> OTHER INFORMATION:

<400> SEQUENCE: 5 tac ttc ccg ccg ccg gct gct aaa gaa gac ttc ctg ggt tgc ctg gtt      48
Tyr Phe Pro Pro Pro Ala Ala Lys Glu Asp Phe Leu Gly Cys Leu Val
1               5                   10                  15 aaa gaa atc ccg ccg cgt ctg ttg tac gcg aaa tcg tcg ccg gcg tat      96
Lys Glu Ile Pro Pro Arg Leu Leu Tyr Ala Lys Ser Ser Pro Ala Tyr
                20                  25                  30 ccc tca gtc ctg ggg cag acc atc cgg aac tcg agg tgg tcg tcg ccg     144
Pro Ser Val Leu Gly Gln Thr Ile Arg Asn Ser Arg Trp Ser Ser Pro
            35                  40                  45 gac aac gtg aag ccg ctc tac atc atc acc ccc acc aac gtc tcc cac     192
Asp Asn Val Lys Pro Leu Tyr Ile Ile Thr Pro Thr Asn Val Ser His
50                  55                  60 atc cag tcc gcc gtg gtg tgc ggc cgc cgc cac agc gtc cgc atc cgc     240
Ile Gln Ser Ala Val Val Cys Gly Arg Arg His Ser Val Arg Ile Arg
65                  70                  75                  80 gtg cgc agc ggc ggg cac gac tac gag ggc ctc tcg tac cgg tct ttg     288
Val Arg Ser Gly Gly His Asp Tyr Glu Gly Leu Ser Tyr Arg Ser Leu
                85                  90                  95 cag ccc gag acg ttc gcc gtc gtc gac ctc aac aag atg cgg gcg gtg     336
Gln Pro Glu Thr Phe Ala Val Val Asp Leu Asn Lys Met Arg Ala Val
            100                 105                 110 tgg gtg gac ggc aag gcc cgc acg gcg tgg gtg gac tcc ggc gcg cag     384
```

-continued

```
                Trp Val Asp Gly Lys Ala Arg Thr Ala Trp Val Asp Ser Gly Ala Gln
                    115                 120                 125 ctc ggc gag ctc tac tac gcc atc tat aag gcg agc ccc acg ctg gcg            432
Leu Gly Glu Leu Tyr Tyr Ala Ile Tyr Lys Ala Ser Pro Thr Leu Ala
130                 135                 140 ttc ccg gcc ggc gtg tgc ccg acg atc gga gtg ggc ggc aac ttc gcg            480
Phe Pro Ala Gly Val Cys Pro Thr Ile Gly Val Gly Gly Asn Phe Ala
145                 150                 155                 160 ggc ggc ggc ttc ggc atg ctg ctc cgc aag tac ggc atc gcc gcg gag            528
Gly Gly Gly Phe Gly Met Leu Leu Arg Lys Tyr Gly Ile Ala Ala Glu
                165                 170                 175 aac gtc atc gac gtg aag ctc gtc gac gcc aac ggc aag ctg cac gac            576
Asn Val Ile Asp Val Lys Leu Val Asp Ala Asn Gly Lys Leu His Asp
            180                 185                 190 aag aag tcc atg ggc gac gac cat ttc tgg gcc gtc agg ggc ggc ggg            624
Lys Lys Ser Met Gly Asp Asp His Phe Trp Ala Val Arg Gly Gly Gly
        195                 200                 205 ggc gag agc ttc ggc atc gtg gtc gcg tgg cag gtg aag ctc ctg ccg            672
Gly Glu Ser Phe Gly Ile Val Val Ala Trp Gln Val Lys Leu Leu Pro
210                 215                 220 gtg ccg ccc acc gtg aca ata ttc aag atc tcc aag aca gtg agc gag            720
Val Pro Pro Thr Val Thr Ile Phe Lys Ile Ser Lys Thr Val Ser Glu
225                 230                 235                 240 ggc gcc gtg gac atc atc aac aag tgg caa gtg gtc gcg ccg cag ctt            768
Gly Ala Val Asp Ile Ile Asn Lys Trp Gln Val Val Ala Pro Gln Leu
                245                 250                 255 ccc gcc gac ctc atg atc cgc atc atc gcg cag ggg ccc aag gcc acg            816
Pro Ala Asp Leu Met Ile Arg Ile Ile Ala Gln Gly Pro Lys Ala Thr
            260                 265                 270 ttc gag gcc atg tac ctc ggc acc tgc aaa acc ctg acg ccg ttg atg            864
Phe Glu Ala Met Tyr Leu Gly Thr Cys Lys Thr Leu Thr Pro Leu Met
        275                 280                 285 agc agc aag ttc ccg gag ctc ggc atg aac ccc tcc cac tgc aac gag            912
Ser Ser Lys Phe Pro Glu Leu Gly Met Asn Pro Ser His Cys Asn Glu
290                 295                 300 atg tca tgg atc cag tcc atc ccc ttc gtc cac ctc ggc cac agg gac            960
Met Ser Trp Ile Gln Ser Ile Pro Phe Val His Leu Gly His Arg Asp
305                 310                 315                 320 gcc ctc gag gac gac ctc ctc aac cgg aac aac tcc ttc aag ccc ttc           1008
Ala Leu Glu Asp Asp Leu Leu Asn Arg Asn Asn Ser Phe Lys Pro Phe
                325                 330                 335 gcc gaa tac aag tcc gac tac gtc tac cag ccc ttc ccc aag acc gtc           1056
Ala Glu Tyr Lys Ser Asp Tyr Val Tyr Gln Pro Phe Pro Lys Thr Val
            340                 345                 350 tgg gag cag atc ctc aac acc tgg ctc gtc aag ccc ggc gcc ggg atc           1104
Trp Glu Gln Ile Leu Asn Thr Trp Leu Val Lys Pro Gly Ala Gly Ile
        355                 360                 365 atg atc ttc gac ccc tac ggc gcc acc atc agc gcc acc ccg gag tcc           1152
Met Ile Phe Asp Pro Tyr Gly Ala Thr Ile Ser Ala Thr Pro Glu Ser
370                 375                 380 gcc acg ccc ttc cct cac cgc aag ggc gtc ctc ttc aac atc cag tac           1200
Ala Thr Pro Phe Pro His Arg Lys Gly Val Leu Phe Asn Ile Gln Tyr
385                 390                 395                 400 gtc aac tac tgg ttc gcc ccg gga gcc gcc gcc gcg ccc ctc tcg tgg           1248
Val Asn Tyr Trp Phe Ala Pro Gly Ala Ala Ala Ala Pro Leu Ser Trp
                405                 410                 415 agc aag gac atc tac aac tac atg gag ccc tac gtg agc aag aac ccc           1296
Ser Lys Asp Ile Tyr Asn Tyr Met Glu Pro Tyr Val Ser Lys Asn Pro
            420                 425                 430 agg cag gcg tac gca aac tac agg gac atc gac ctc ggc agg aac gag           1344
Arg Gln Ala Tyr Ala Asn Tyr Arg Asp Ile Asp Leu Gly Arg Asn Glu
```

```
Arg Gln Ala Tyr Ala Asn Tyr Arg Asp Ile Asp Leu Gly Arg Asn Glu
        435                 440                 445 gtg gtc aac gac gtc tcc acc tac gcc agc ggc aag gtc tgg ggc cag      1392
Val Val Asn Asp Val Ser Thr Tyr Ala Ser Gly Lys Val Trp Gly Gln
        450                 455                 460 aaa tac ttc aag ggc aac ttc gag agg ctc gcc att acc aag ggc aag      1440
Lys Tyr Phe Lys Gly Asn Phe Glu Arg Leu Ala Ile Thr Lys Gly Lys
465                 470                 475                 480 gtc gat cct acc gac tac ttc agg aac gag cag agc atc ccg ccg ctc      1488
Val Asp Pro Thr Asp Tyr Phe Arg Asn Glu Gln Ser Ile Pro Pro Leu
                485                 490                 495 atc aaa aag tac tga                                                  1503
Ile Lys Lys Tyr
        500

<210> SEQ ID NO 6
<211> LENGTH: 500
<212> TYPE: PRT
<213> ORGANISM: Phleum pratense

<400> SEQUENCE: 6

Tyr Phe Pro Pro Ala Ala Lys Glu Asp Phe Leu Gly Cys Leu Val
1               5                   10                  15

Lys Glu Ile Pro Pro Arg Leu Leu Tyr Ala Lys Ser Ser Pro Ala Tyr
            20                  25                  30

Pro Ser Val Leu Gly Gln Thr Ile Arg Asn Ser Arg Trp Ser Ser Pro
        35                  40                  45

Asp Asn Val Lys Pro Leu Tyr Ile Ile Thr Pro Thr Asn Val Ser His
    50                  55                  60

Ile Gln Ser Ala Val Val Cys Gly Arg Arg His Ser Val Arg Ile Arg
65                  70                  75                  80

Val Arg Ser Gly Gly His Asp Tyr Glu Gly Leu Ser Tyr Arg Ser Leu
                85                  90                  95

Gln Pro Glu Thr Phe Ala Val Val Asp Leu Asn Lys Met Arg Ala Val
            100                 105                 110

Trp Val Asp Gly Lys Ala Arg Thr Ala Trp Val Asp Ser Gly Ala Gln
        115                 120                 125

Leu Gly Glu Leu Tyr Tyr Ala Ile Tyr Lys Ala Ser Pro Thr Leu Ala
130                 135                 140

Phe Pro Ala Gly Val Cys Pro Thr Ile Gly Val Gly Gly Asn Phe Ala
145                 150                 155                 160

Gly Gly Gly Phe Gly Met Leu Leu Arg Lys Tyr Gly Ile Ala Ala Glu
                165                 170                 175

Asn Val Ile Asp Val Lys Leu Val Asp Ala Asn Gly Lys Leu His Asp
            180                 185                 190

Lys Lys Ser Met Gly Asp Asp His Phe Trp Ala Val Arg Gly Gly Gly
        195                 200                 205

Gly Glu Ser Phe Gly Ile Val Val Ala Trp Gln Val Lys Leu Leu Pro
    210                 215                 220

Val Pro Pro Thr Val Thr Ile Phe Lys Ile Ser Lys Thr Val Ser Glu
225                 230                 235                 240

Gly Ala Val Asp Ile Ile Asn Lys Trp Gln Val Val Ala Pro Gln Leu
                245                 250                 255

Pro Ala Asp Leu Met Ile Arg Ile Ile Ala Gln Gly Pro Lys Ala Thr
            260                 265                 270

Phe Glu Ala Met Tyr Leu Gly Thr Cys Lys Thr Leu Thr Pro Leu Met
        275                 280                 285
```

```
Ser Ser Lys Phe Pro Glu Leu Gly Met Asn Pro Ser His Cys Asn Glu
    290                 295                 300

Met Ser Trp Ile Gln Ser Ile Pro Phe Val His Leu Gly His Arg Asp
305                 310                 315                 320

Ala Leu Glu Asp Asp Leu Leu Asn Arg Asn Asn Ser Phe Lys Pro Phe
                325                 330                 335

Ala Glu Tyr Lys Ser Asp Tyr Val Tyr Gln Pro Phe Pro Lys Thr Val
            340                 345                 350

Trp Glu Gln Ile Leu Asn Thr Trp Leu Val Lys Pro Gly Ala Gly Ile
        355                 360                 365

Met Ile Phe Asp Pro Tyr Gly Ala Thr Ile Ser Ala Thr Pro Glu Ser
370                 375                 380

Ala Thr Pro Phe Pro His Arg Lys Gly Val Leu Phe Asn Ile Gln Tyr
385                 390                 395                 400

Val Asn Tyr Trp Phe Ala Pro Gly Ala Ala Ala Pro Leu Ser Trp
                405                 410                 415

Ser Lys Asp Ile Tyr Asn Tyr Met Glu Pro Tyr Val Ser Lys Asn Pro
                420                 425                 430

Arg Gln Ala Tyr Ala Asn Tyr Arg Asp Ile Asp Leu Gly Arg Asn Glu
            435                 440                 445

Val Val Asn Asp Val Ser Thr Tyr Ala Ser Gly Lys Val Trp Gly Gln
    450                 455                 460

Lys Tyr Phe Lys Gly Asn Phe Glu Arg Leu Ala Ile Thr Lys Gly Lys
465                 470                 475                 480

Val Asp Pro Thr Asp Tyr Phe Arg Asn Glu Gln Ser Ile Pro Pro Leu
                485                 490                 495

Ile Lys Lys Tyr
        500

<210> SEQ ID NO 7
<211> LENGTH: 10
<212> TYPE: PRT
<213> ORGANISM: Phleum pratense
<220> FEATURE:
<221> NAME/KEY: MISC_FEATURE
<222> LOCATION: (6)..(6)
<223> OTHER INFORMATION: undetermined amino acid

<400> SEQUENCE: 7

Ile Val Ala Leu Pro Xaa Gly Met Leu Lys
1               5                   10

<210> SEQ ID NO 8
<211> LENGTH: 14
<212> TYPE: PRT
<213> ORGANISM: Lolium perenne

<400> SEQUENCE: 8

Phe Leu Glu Pro Val Leu Gly Leu Ile Phe Pro Ala Gly Val
1               5                   10

<210> SEQ ID NO 9
<211> LENGTH: 9
<212> TYPE: PRT
<213> ORGANISM: Lolium perenne

<400> SEQUENCE: 9

Gly Leu Ile Glu Phe Pro Ala Gly Val
1               5
```

<210> SEQ ID NO 10
<211> LENGTH: 12
<212> TYPE: PRT
<213> ORGANISM: Dactylus glomerata

<400> SEQUENCE: 10

Asp Ile Tyr Asn Tyr Met Glu Pro Tyr Val Ser Lys
1               5                   10

<210> SEQ ID NO 11
<211> LENGTH: 11
<212> TYPE: PRT
<213> ORGANISM: Dactylus glomerata

<400> SEQUENCE: 11

Val Asp Pro Thr Asp Tyr Phe Gly Asn Glu Gln
1               5                   10

<210> SEQ ID NO 12
<211> LENGTH: 17
<212> TYPE: PRT
<213> ORGANISM: Dactylus glomerata

<400> SEQUENCE: 12

Ala Arg Thr Ala Trp Val Asp Ser Gly Ala Gln Leu Gly Glu Leu Ser
1               5                   10                  15

Tyr

<210> SEQ ID NO 13
<211> LENGTH: 15
<212> TYPE: PRT
<213> ORGANISM: Dactylus glomerata

<400> SEQUENCE: 13

Gly Val Leu Phe Asn Ile Gln Tyr Val Asn Tyr Trp Phe Ala Pro
1               5                   10                  15

<210> SEQ ID NO 14
<211> LENGTH: 11
<212> TYPE: PRT
<213> ORGANISM: Cynodon dactylon

<400> SEQUENCE: 14

Lys Thr Val Lys Pro Leu Tyr Ile Ile Thr Pro
1               5                   10

<210> SEQ ID NO 15
<211> LENGTH: 22
<212> TYPE: PRT
<213> ORGANISM: Cynodon dactylon

<400> SEQUENCE: 15

Lys Gln Val Glu Arg Asp Phe Leu Thr Ser Leu Thr Lys Asp Ile Pro
1               5                   10                  15

Gln Leu Tyr Leu Lys Ser
            20

<210> SEQ ID NO 16
<211> LENGTH: 16
<212> TYPE: PRT
<213> ORGANISM: Cynodon dactylon

<400> SEQUENCE: 16

Thr Val Lys Pro Leu Tyr Ile Ile Thr Pro Ile Thr Ala Ala Met Ile

-continued

<210> SEQ ID NO 17
<211> LENGTH: 24
<212> TYPE: PRT
<213> ORGANISM: Cynodon dactylon

<400> SEQUENCE: 17

Leu Arg Lys Tyr Gly Thr Ala Ala Asp Asn Val Ile Asp Ala Lys Val
1               5                   10                  15

Val Asp Ala Gln Gly Arg Leu Leu
            20

<210> SEQ ID NO 18
<211> LENGTH: 14
<212> TYPE: PRT
<213> ORGANISM: Cynodon dactylon

<400> SEQUENCE: 18

Lys Trp Gln Thr Val Ala Pro Ala Leu Pro Asp Pro Asn Met
1               5                   10

<210> SEQ ID NO 19
<211> LENGTH: 15
<212> TYPE: PRT
<213> ORGANISM: Cynodon dactylon

<400> SEQUENCE: 19

Val Thr Trp Ile Glu Ser Val Pro Tyr Ile Pro Met Gly Asp Lys
1               5                   10                  15

<210> SEQ ID NO 20
<211> LENGTH: 19
<212> TYPE: PRT
<213> ORGANISM: Cynodon dactylon
<220> FEATURE:
<221> NAME/KEY: MISC_FEATURE
<222> LOCATION: (8)..(8)
<223> OTHER INFORMATION: undetermined amino acid

<400> SEQUENCE: 20

Gly Thr Val Arg Gln Leu Leu Xaa Arg Thr Ser Asn Ile Lys Ala Phe
1               5                   10                  15

Gly Lys Tyr

<210> SEQ ID NO 21
<211> LENGTH: 23
<212> TYPE: PRT
<213> ORGANISM: Cynodon dactylon

<400> SEQUENCE: 21

Thr Ser Asn Ile Lys Ala Phe Gly Lys Tyr Lys Ser Asp Tyr Val Leu
1               5                   10                  15

Glu Pro Ile Pro Lys Lys Ser
            20

<210> SEQ ID NO 22
<211> LENGTH: 13
<212> TYPE: PRT
<213> ORGANISM: Cynodon dactylon

<400> SEQUENCE: 22

Tyr Arg Asp Leu Asp Leu Gly Val Asn Gln Val Val Gly
1               5                   10

```
<210> SEQ ID NO 23
<211> LENGTH: 15
<212> TYPE: PRT
<213> ORGANISM: Cynodon dactylon

<400> SEQUENCE: 23

Ser Ala Thr Pro Pro Thr His Arg Ser Gly Val Leu Phe Asn Ile
1               5                   10                  15

<210> SEQ ID NO 24
<211> LENGTH: 36
<212> TYPE: PRT
<213> ORGANISM: Cynodon dactylon

<400> SEQUENCE: 24

Ala Ala Ala Ala Leu Pro Thr Gln Val Thr Arg Asp Ile Tyr Ala Phe
1               5                   10                  15

Met Thr Pro Tyr Val Ser Lys Asn Pro Arg Gln Ala Tyr Val Asn Tyr
            20                  25                  30

Arg Asp Leu Asp
        35

<210> SEQ ID NO 25
<211> LENGTH: 149
<212> TYPE: DNA
<213> ORGANISM: Phleum pratense

<400> SEQUENCE: 25
caccggaagg gggtgctgtt caacatccag tacgtcaact actggttcgc cccgggagcc    60
ggcgcggcgc cattgtcgtg gagcaaggag atctacaact acatggagcc gtacgtgagc   120
aaggaccccg tccaggccta cgccaacta                                     149

<210> SEQ ID NO 26
<211> LENGTH: 299
<212> TYPE: DNA
<213> ORGANISM: Phleum pratense

<400> SEQUENCE: 26
actactggtt cgccccggga gccggcgcgg cgccattgtc gtggagcaag gagatctaca    60
actacatgga gccatacgtg agcaagaacc ccaggcaggc ctacgccaac tagggacta   120 tcgacctcgg gaggaacgag gtggtgaacg acgtctccac cttcagcagc ggtttggtgt   180
ggggccagaa atacttcaag ggcaacttcc agaggctcgc catcaccaag gcaaggtgg   240 atcccaccga ctacttcagg aacgagcaga gcatcccgcc gctcatcaaa agtactga    299

<210> SEQ ID NO 27
<211> LENGTH: 33
<212> TYPE: PRT
<213> ORGANISM: Phleum pratense
<220> FEATURE:
<221> NAME/KEY: MISC_FEATURE
<222> LOCATION: (14)..(14)
<223> OTHER INFORMATION: undetermined amino acid

<400> SEQUENCE: 27

Tyr Phe Pro Pro Pro Ala Ala Lys Glu Asp Phe Leu Gly Xaa Leu Val
1               5                   10                  15

Lys Glu Ile Pro Pro Arg Leu Leu Tyr Ala Lys Ser Ser Pro Ala Tyr
            20                  25                  30

Pro
```

<210> SEQ ID NO 28
<211> LENGTH: 18
<212> TYPE: PRT
<213> ORGANISM: Phleum pratense
<220> FEATURE:
<221> NAME/KEY: MISC_FEATURE
<222> LOCATION: (6)..(6)
<223> OTHER INFORMATION: undetermined amino acid

<400> SEQUENCE: 28

Ser Ala Thr Pro Phe Xaa His Arg Lys Gly Val Leu Phe Asn Ile Gln
1               5                   10                  15

Tyr Val

<210> SEQ ID NO 29
<211> LENGTH: 10
<212> TYPE: PRT
<213> ORGANISM: Phleum pratense
<220> FEATURE:
<221> NAME/KEY: MISC_FEATURE
<222> LOCATION: (3)..(8)
<223> OTHER INFORMATION: undetermined amino acid

<400> SEQUENCE: 29

Gly Leu Xaa Tyr Arg Xaa Leu Xaa Pro Glu
1               5                   10

<210> SEQ ID NO 30
<211> LENGTH: 12
<212> TYPE: PRT
<213> ORGANISM: Phleum pratense
<220> FEATURE:
<221> NAME/KEY: MISC_FEATURE
<222> LOCATION: (2)..(9)
<223> OTHER INFORMATION: undetermined amino acid

<400> SEQUENCE: 30

Lys Xaa Met Gly Asp Asp His Phe Xaa Ala Val Arg
1               5                   10

<210> SEQ ID NO 31
<211> LENGTH: 9
<212> TYPE: PRT
<213> ORGANISM: Phleum pratense

<400> SEQUENCE: 31

Ala Pro Glu Gly Ala Val Asp Ile Ile
1               5

<210> SEQ ID NO 32
<211> LENGTH: 16
<212> TYPE: PRT
<213> ORGANISM: Phleum pratense

<400> SEQUENCE: 32

Met Glu Pro Tyr Val Ser Ile Asn Pro Val Gln Ala Tyr Ala Asn Tyr
1               5                   10                  15

<210> SEQ ID NO 33
<211> LENGTH: 15
<212> TYPE: PRT
<213> ORGANISM: Phleum pratense
<220> FEATURE:
<221> NAME/KEY: MISC_FEATURE
<222> LOCATION: (14)..(14)
<223> OTHER INFORMATION: undetermined amino acid

<400> SEQUENCE: 33

-continued

Tyr Phe Pro Pro Pro Ala Ala Lys Glu Asp Phe Leu Gly Xaa Leu
1               5                   10                  15

<210> SEQ ID NO 34
<211> LENGTH: 10
<212> TYPE: PRT
<213> ORGANISM: Phleum pratense

<400> SEQUENCE: 34

Leu Tyr Ala Lys Ser Ser Pro Ala Tyr Pro
1               5                   10

<210> SEQ ID NO 35
<211> LENGTH: 33
<212> TYPE: PRT
<213> ORGANISM: Phleum pratense
<220> FEATURE:
<221> NAME/KEY: MISC_FEATURE
<222> LOCATION: (14)..(14)
<223> OTHER INFORMATION: undetermined amino acid

<400> SEQUENCE: 35

Tyr Phe Pro Pro Pro Ala Ala Lys Glu Asp Phe Leu Gly Xaa Leu Val
1               5                   10                  15

Lys Glu Ile Pro Pro Arg Leu Leu Tyr Ala Lys Ser Ser Pro Ala Tyr
                20                  25                  30

Pro

<210> SEQ ID NO 36
<211> LENGTH: 29
<212> TYPE: PRT
<213> ORGANISM: Phleum pratense
<220> FEATURE:
<221> NAME/KEY: MISC_FEATURE
<222> LOCATION: (14)..(14)
<223> OTHER INFORMATION: undetermined amino acid

<400> SEQUENCE: 36

Tyr Phe Pro Pro Pro Ala Ala Lys Glu Asp Phe Leu Gly Xaa Leu Val
1               5                   10                  15

Lys Glu Pro Pro Arg Leu Leu Tyr Ala Lys Ser Ser Pro
                20                  25

<210> SEQ ID NO 37
<211> LENGTH: 15
<212> TYPE: PRT
<213> ORGANISM: Phleum pratense
<220> FEATURE:
<221> NAME/KEY: MISC_FEATURE
<222> LOCATION: (4)..(14)
<223> OTHER INFORMATION: undetermined amino acid

<400> SEQUENCE: 37

Tyr Phe Pro Xaa Xaa Ala Ala Lys Glu Asp Phe Leu Gly Xaa Leu
1               5                   10                  15

<210> SEQ ID NO 38
<211> LENGTH: 15
<212> TYPE: PRT
<213> ORGANISM: Phleum pratense
<220> FEATURE:
<221> NAME/KEY: MISC_FEATURE
<222> LOCATION: (4)..(14)
<223> OTHER INFORMATION: undetermined amino acid

<400> SEQUENCE: 38

```
Tyr Phe Pro Xaa Xaa Ala Lys Lys Glu Asp Phe Leu Gly Xaa Leu
1               5                   10                  15
```

<210> SEQ ID NO 39
<211> LENGTH: 15
<212> TYPE: PRT
<213> ORGANISM: Phleum pratense
<220> FEATURE:
<221> NAME/KEY: MISC_FEATURE
<222> LOCATION: (4)..(14)
<223> OTHER INFORMATION: undetermined amino acid

<400> SEQUENCE: 39

```
Tyr Phe Pro Xaa Xaa Ala Ala Lys Asp Asp Phe Leu Gly Xaa Leu
1               5                   10                  15
```

<210> SEQ ID NO 40
<211> LENGTH: 11
<212> TYPE: PRT
<213> ORGANISM: Phleum pratense
<220> FEATURE:
<221> NAME/KEY: MISC_FEATURE
<222> LOCATION: (4)..(5)
<223> OTHER INFORMATION: undetermined amino acid

<400> SEQUENCE: 40

```
Tyr Phe Pro Xaa Xaa Leu Ala Asn Glu Asp Phe
1               5                   10
```

<210> SEQ ID NO 41
<211> LENGTH: 18
<212> TYPE: PRT
<213> ORGANISM: Phleum pratense
<220> FEATURE:
<221> NAME/KEY: MISC_FEATURE
<222> LOCATION: (6)..(6)
<223> OTHER INFORMATION: undetermined amino acid

<400> SEQUENCE: 41

```
Ser Ala Thr Pro Phe Xaa His Arg Lys Gly Val Leu Phe Asn Ile Gln
1               5                   10                  15

Tyr Val
```

<210> SEQ ID NO 42
<211> LENGTH: 10
<212> TYPE: PRT
<213> ORGANISM: Phleum pratense
<220> FEATURE:
<221> NAME/KEY: MISC_FEATURE
<222> LOCATION: (3)..(8)
<223> OTHER INFORMATION: undetermined amino acid

<400> SEQUENCE: 42

```
Gly Leu Xaa Tyr Arg Xaa Leu Xaa Pro Glu
1               5                   10
```

<210> SEQ ID NO 43
<211> LENGTH: 12
<212> TYPE: PRT
<213> ORGANISM: Phleum pratense
<220> FEATURE:
<221> NAME/KEY: MISC_FEATURE
<222> LOCATION: (2)..(9)
<223> OTHER INFORMATION: undetermined amino acid

<400> SEQUENCE: 43

```
Lys Xaa Met Gly Asp Asp His Phe Xaa Ala Val Arg
1               5                   10
```

```
<210> SEQ ID NO 44
<211> LENGTH: 9
<212> TYPE: PRT
<213> ORGANISM: Phleum pratense

<400> SEQUENCE: 44

Ala Pro Glu Gly Ala Val Asp Ile Ile
1               5

<210> SEQ ID NO 45
<211> LENGTH: 16
<212> TYPE: PRT
<213> ORGANISM: Phleum pratense

<400> SEQUENCE: 45

Met Glu Pro Tyr Val Ser Ile Asn Pro Val Gln Ala Tyr Ala Asn Tyr
1               5                   10                  15

<210> SEQ ID NO 46
<211> LENGTH: 29
<212> TYPE: DNA
<213> ORGANISM: Phleum pratense
<220> FEATURE:
<221> NAME/KEY: misc_feature
<222> LOCATION: (1)..(29)
<223> OTHER INFORMATION: 'n' means inosin

<400> SEQUENCE: 46
ytntaygcna arwsnwsncc ngcntaycc                                  29

<210> SEQ ID NO 47
<211> LENGTH: 28
<212> TYPE: DNA
<213> ORGANISM: Phleum pratense
<220> FEATURE:
<221> NAME/KEY: misc_feature
<222> LOCATION: (1)..(28)
<223> OTHER INFORMATION: 'n' means inosin

<400> SEQUENCE: 47
caymgnaarg gngtnytntt yaayatmc                                   28

<210> SEQ ID NO 48
<211> LENGTH: 26
<212> TYPE: DNA
<213> ORGANISM: Phleum pratense
<220> FEATURE:
<221> NAME/KEY: misc_feature
<222> LOCATION: (1)..(26)
<223> OTHER INFORMATION: 'n' means inosin

<400> SEQUENCE: 48
tarttngcrt angcytgnac nggrtt                                     26

<210> SEQ ID NO 49
<211> LENGTH: 23
<212> TYPE: DNA
<213> ORGANISM: Phleum pratense

<400> SEQUENCE: 49
actactggtt cgccccggga gcc                                        23

<210> SEQ ID NO 50
<211> LENGTH: 28
<212> TYPE: DNA
<213> ORGANISM: Phleum pratense
```

```
<400> SEQUENCE: 50
tgaagtattt ctggccccac accaaacc                                          28

<210> SEQ ID NO 51
<211> LENGTH: 24
<212> TYPE: DNA
<213> ORGANISM: Phleum pratense

<400> SEQUENCE: 51
cccttggtga tggcgagcct ctgg                                              24

<210> SEQ ID NO 52
<211> LENGTH: 23
<212> TYPE: DNA
<213> ORGANISM: Phleum pratense

<400> SEQUENCE: 52
ctcagtcctg gggcagacca tcc                                               23
```